(12) United States Patent
Marnfeldt et al.

(10) Patent No.: US 10,806,930 B2
(45) Date of Patent: *Oct. 20, 2020

(54) DETERMINING AND FORECASTING END OF LIFE FOR AN IMPLANTABLE MEDICAL DEVICE HAVING A RECHARGEABLE BATTERY

(71) Applicant: Boston Scientific Neuromodulation Corporation, Valencia, CA (US)

(72) Inventors: Goran N. Marnfeldt, Valencia, CA (US); Rafael Carbunaru, Valley Village, CA (US); Jordi Parramon, Valencia, CA (US)

(73) Assignee: Boston Scientific Neuromodulation Corporation, Valencia, CA (US)

(*) Notice: Subject to any disclaimer, the term of this patent is extended or adjusted under 35 U.S.C. 154(b) by 278 days.

This patent is subject to a terminal disclaimer.

(21) Appl. No.: 15/879,095

(22) Filed: Jan. 24, 2018

(65) Prior Publication Data

US 2018/0152025 A1    May 31, 2018

Related U.S. Application Data

(63) Continuation of application No. 15/266,669, filed on Sep. 15, 2016, now Pat. No. 9,887,573, which is a (Continued)

(51) Int. Cl.
*A61N 1/378* (2006.01)
*A61N 1/36* (2006.01)
(Continued)

(52) U.S. Cl.
CPC ......... *A61N 1/36128* (2013.01); *A61N 1/378* (2013.01); *G01R 31/3648* (2013.01);
(Continued)

(58) Field of Classification Search
CPC .................................................... A61N 1/3708
See application file for complete search history.

(56) References Cited

U.S. PATENT DOCUMENTS 5,391,193 A    2/1995  Thompson
6,016,448 A *  1/2000  Busacker ............. A61N 1/3708
                                                    607/29
(Continued)

FOREIGN PATENT DOCUMENTS

CN    101389377    4/2009
WO    2009/091407  7/2009

*Primary Examiner* — George R Evanisko
(74) *Attorney, Agent, or Firm* — Lewis & Reese, PLLC

(57) ABSTRACT

An algorithm programmed into the control circuitry of a rechargeable-battery Implantable Medical Device (IMD) is disclosed that can quantitatively forecast and determine the timing of an early replacement indicator (tEOLi) and an IMD End of Life (tEOL). These forecasts and determinations of tEOLi and tEOL occur in accordance with one or more parameters having an effect on rechargeable battery capacity, such as number of charging cycles, charging current, discharge depth, load current, and battery calendar age. The algorithm consults such parameters as stored over the history of the operation of the IMD in a parameter log, and in conjunction with a battery capacity database reflective of the effect of these parameters on battery capacity, determines and forecasts tEOLi and tEOL. Such forecasted or determined values may also be used by a shutdown algorithm to suspend therapeutic operation of the IMD.

20 Claims, 12 Drawing Sheets

Related U.S. Application Data continuation of application No. 14/593,742, filed on Jan. 9, 2015, now Pat. No. 9,446,244.

(60) Provisional application No. 61/928,391, filed on Jan. 16, 2014.

(51) Int. Cl.

| | | |
|---|---|---|
| *G01R 31/392* | (2019.01) | |
| *G01R 31/36* | (2020.01) | |
| *H02J 7/00* | (2006.01) | |
| *A61N 1/37* | (2006.01) | |

(52) U.S. Cl.
CPC ............ *G01R 31/392* (2019.01); *H02J 7/00* (2013.01); *H02J 7/007* (2013.01); *H02J 7/0047* (2013.01); *A61N 1/3708* (2013.01); *H02J 7/00034* (2020.01); *H02J 7/0048* (2020.01)

(56) References Cited

U.S. PATENT DOCUMENTS

| | | |
|---|---|---|
| 6,020,778 A | 2/2000 | Shigehara et al. |
| 6,516,227 B1 | 2/2003 | Meadows et al. |
| 7,123,964 B2 | 10/2006 | Betzold et al. |
| 7,177,690 B2 * | 2/2007 | Woods ............... A61N 1/36071 607/29 |
| 7,177,698 B2 | 2/2007 | Klosterman et al. |
| 7,962,222 B2 | 6/2011 | He et al. |
| 8,193,766 B2 | 6/2012 | Rondoni et al. |
| 8,620,431 B2 | 12/2013 | Fuller et al. |
| 8,649,858 B2 | 2/2014 | Griffith et al. |
| 8,666,504 B2 | 3/2014 | Dronov et al. |
| 8,744,592 B2 | 6/2014 | Carbunaru et al. |
| 8,761,885 B2 * | 6/2014 | Hussain ............... A61N 1/378 607/29 |
| 8,781,596 B2 | 7/2014 | Aghassian et al. |
| 2005/0266301 A1 | 12/2005 | Smith |
| 2007/0179549 A1 | 8/2007 | Russie |
| 2008/0097544 A1 | 4/2008 | Gandhi et al. |
| 2008/0306569 A1 * | 12/2008 | Tobacman ........... A61N 1/3708 607/29 |
| 2008/0312852 A1 | 12/2008 | Maack |
| 2009/0182517 A1 | 7/2009 | Gandhi et al. |
| 2012/0049802 A1 | 3/2012 | Barsukov et al. |
| 2012/0095529 A1 | 4/2012 | Parramon et al. |
| 2012/0197341 A1 | 8/2012 | Cowley |
| 2013/0023943 A1 | 1/2013 | Parramon et al. |
| 2013/0096651 A1 | 4/2013 | Ozawa et al. |
| 2013/0193912 A1 | 8/2013 | Bornhoft |
| 2014/0249603 A1 | 9/2014 | Yan et al. |
| 2015/0066110 A1 | 3/2015 | Tahmasian |
| 2015/0080982 A1 | 3/2015 | Funderburk |
| 2015/0105842 A1 | 4/2015 | Lamont et al. |

* cited by examiner

| Charging session (Nc) | Timestamp | Charging time (Tc) (min) | Vbat(i) | Vbat(f) | ΔVbat= Vbat(f)- Vbat(i) | Ibat (mA) | Charge (Cc) = Ibat*Tc |
|---|---|---|---|---|---|---|---|
| 1 | t1 | 13.2 | 2.5 | 4.15 | 1.65 | 40 | 528 |
| 2 | t3 | 6.6 | 3.3 | 4.1 | 0.8 | 40 | 264 |
| 3 | t5 | 13.0 | 3.45 | 4.15 | 1.7 | 40 | 520 |
| 4 | t7 | 14.1 | 2.2 | 4.2 | 2.0 | 37 | 518 |
| 5 | t9 | 8.7 | 3.0 | 4.1 | 1.1 | 40 | 348 |
| 6 | t11 | 12.6 | 2.5 | 4.15 | 1.65 | 40 | 504 |
| ⋮ | | | | | | | |
| 104 | t207 | 13.4 | 4.1 | 1.5 | 2.6 | 36 | 482 |
| 105 | t209 | 14.0 | 4.0 | 1.8 | 2.2 | 34 | 476 |
| 106 | t211 | 12.9 | 4.05 | 1.75 | 2.3 | 36 | 464 |

⟩ 120c

| Use Session (Nu) | Timestamp | Use time (Tu) (min) | Iload (mA) | Charge (Cu) = Iload*Tu |
|---|---|---|---|---|
| 1 | t0 | Tu1 | Iload1 | Cu1 |
| 2 | t2 | Tu2 | Iload2 | Cu2 |
| 3 | t4 | Tu3 | Iload3 | Cu3 |
| 4 | t6 | Tu4 | Iload4 | Cu4 |
| 5 | t8 | Tu5 | Iload5 | Cu5 |
| 6 | t10 | Tu6 | Iload6 | Cu6 |
| ⋮ | | | | |
| 104 | t206 | 13.4 | Iload 104 | Cu104 |
| 105 | t208 | 14.0 | Iload105 | Cu105 |
| 106 | t210 | 12.9 | Iload106 | Cu106 |

⟩ 120u

| Calendar age (A) |
|---|
| tcurrent |

⟩ 120a

Capacity-relevant parameter log 120

*Figure 5A*

Present capacity-relevant parameters 120'

| Cc(tot) | Nc | ΔVbat(avg) | Ibat(avg) | Cu(tot) | Iload(avg) | Calendar age (A) | Charge ratio (Z) = Cu(tot)/Cc(tot) |
|---|---|---|---|---|---|---|---|
| Cc(tot)2 | Nc4 | ΔVbat(avg)3 | Ibat(avg)6 | Cu(tot)2 | Iload(avg)4 | A3 | Z2 |

*Figure 5B*

Battery capacity database 122

| Cc(tot) | Nc | ΔVbat(avg) | Ibat(avg) | Cu(tot) | Iload(avg) | Calendar age (A) | Charge ratio (Z) | % change in battery capacity |
|---|---|---|---|---|---|---|---|---|
| Cc(tot)1 | Nc1 | ΔVbat(avg)1 | Ibat(avg)1 | Cu(tot)1 | Iload(avg)1 | t1 | R3 | -X1% |
| Cc(tot)2 | Nc2 | ΔVbat(avg)2 | Ibat(avg)2 | Cu(tot)2 | Iload(avg)2 | t2 | R2 | -X2% |
| Cc(tot)3 | Nc3 | ΔVbat(avg)3 | Ibat(avg)3 | Cu(tot)3 | Iload(avg)3 | t3 | R1 | -X3% |

| | Cc(tot) | Nc | ΔVbat(avg) | Ibat(avg) | Cu(tot) | Iload(avg) | Calendar age (A) | Charge ratio (Z) |
|---|---|---|---|---|---|---|---|---|
| Weight | 1 | 0.3 | 0.5 | 0.1 | 0.6 | 0.15 | 0.2 | 0.8 |
| Priority | 1 | 5 | 4 | 8 | 3 | 7 | 6 | 2 |

*Figure 5C*

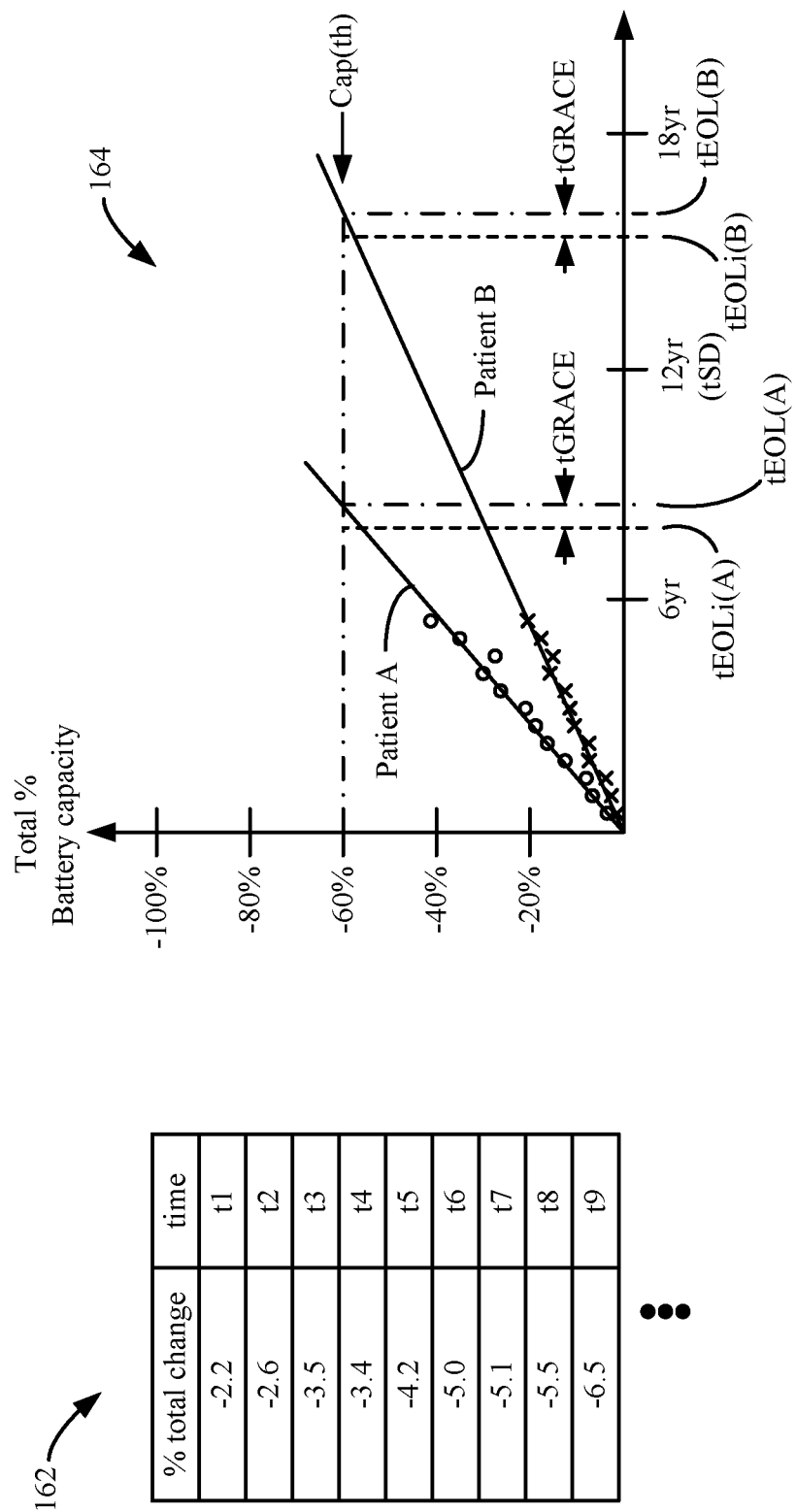

DETERMINING AND FORECASTING END OF LIFE FOR AN IMPLANTABLE MEDICAL DEVICE HAVING A RECHARGEABLE BATTERY

CROSS REFERENCE TO RELATED APPLICATIONS

This application is a continuation of U.S. application Ser. No. 15/266,669, filed Sep. 15, 2016 (now U.S. Pat. No. 9,887,573), which is a continuation of U.S. application Ser. No. 14/593,742, filed Jan. 9, 2015 (now U.S. Pat. No. 9,446,244), which is a non-provisional of U.S. Provisional Patent Application Ser. No. 61/928,391, filed Jan. 16, 2014. Priority is claimed to these applications, and they are incorporated herein by reference in their entireties.

This application is related to U.S. Patent Application Publications 2015/0196768 and 2015/0196764 (both currently pending), which are both incorporated herein by reference in their entireties.

FIELD OF THE INVENTION

This application relates to the field of implantable medical devices, and in particular to rechargeable battery implantable medical devices.

BACKGROUND

Implantable stimulation devices deliver electrical stimuli to nerves and tissues for the therapy of various biological disorders, such as pacemakers to treat cardiac arrhythmia, defibrillators to treat cardiac fibrillation, cochlear stimulators to treat deafness, retinal stimulators to treat blindness, muscle stimulators to produce coordinated limb movement, spinal cord stimulators to treat chronic pain, cortical and deep brain stimulators to treat motor and psychological disorders, and other neural stimulators to treat urinary incontinence, sleep apnea, shoulder subluxation, etc. The description that follows will generally focus on the use of the invention within a Spinal Cord Stimulation (SCS) system, such as that disclosed in U.S. Pat. No. 6,516,227. However, the present invention may find applicability with any implantable medical device or in any implantable medical device system.

An SCS system typically includes an Implantable Pulse Generator (IPG) 10 shown in plan and cross-sectional views in FIGS. 1A and 1B. The IPG 10 includes a biocompatible device case 30 that holds the circuitry and battery 36 necessary for the IPG to function. The IPG 10 is coupled to electrodes 16 via one or more electrode leads 14 that form an electrode array 12. The electrodes 16 are configured to contact a patient's tissue and are carried on a flexible body 18, which also houses the individual lead wires 20 coupled to each electrode 16. The lead wires 20 are also coupled to proximal contacts 22, which are insertable into lead connectors 24 fixed in a header 28 on the IPG 10, which header can comprise an epoxy for example. Once inserted, the proximal contacts 22 connect to header contacts 26, which are in turn coupled by feedthrough pins 34 through a case feedthrough 32 to circuitry within the case 30.

In the illustrated IPG 10, there are thirty-two lead electrodes (E1-E32) split between four leads 14, with the header 28 containing a 2×2 array of lead connectors 24. However, the number of leads and electrodes in an IPG is application specific and therefore can vary. In a SCS application, the electrode leads 14 are typically implanted proximate to the dura in a patient's spinal cord, and when a four-lead IPG 10 is used, these leads are usually split with two on each of the right and left sides of the dura. The proximal electrodes 22 are tunneled through the patient's tissue to a distant location such as the buttocks where the IPG case 30 is implanted, at which point they are coupled to the lead connectors 24. A four-lead IPG 10 can also be used for Deep Brain Stimulation (DBS) in another example. In other IPG examples designed for implantation directly at a site requiring stimulation, the IPG can be lead-less, having electrodes 16 instead appearing on the body of the IPG for contacting the patient's tissue.

As shown in the cross section of FIG. 1B, the IPG 10 includes a printed circuit board (PCB) 40. Electrically coupled to the PCB 40 are the battery 36, which in this example is rechargeable; other circuitry 50a and 50b coupled to top and bottom surfaces of the PCB; a telemetry coil 42 for wirelessly communicating with an external controller (not shown) using telemetry modulation/demodulation circuitry 43 (FIG. 2); a charging coil 44 for wirelessly receiving a magnetic charging field from an external charger 90 (FIG. 2) for recharging the battery 36; and the feedthrough pins 34 (connection not shown). If battery 36 is permanent and not rechargeable, charging coil 44 would be unnecessary. (Further details concerning operation of the coils 42 and 44 and the external devices with which they communicate can be found in U.S. Patent Application Publication 2015/0080982.

Battery management circuitry 84 for the rechargeable battery 36 in the IPG 10 is described in one example in commonly-owned U.S. Patent Application Publication 2013/0023943, which is incorporated herein by reference in its entirety, and shown in FIG. 2. Rechargeable battery 36 may comprise a Li-ion polymer battery, which when fully charged can provide a voltage (Vbat=Vmax) of about 4.2 Volts. However, other rechargeable battery chemistries could be used for battery 36 as well.

An external charger 90, typically a hand-held, battery-powered device, produces a magnetic non-data modulated charging field 98 (e.g., 80 kHz) from a coil 92. The magnetic field 98 is met in the IPG 10 by front-end charging circuitry 96, where it energizes the charging coil 44 by inducing a current in the coil. The induced current is processed by rectifier circuitry 46, including a rectifier and optionally a filtering capacitor and a voltage-magnitude-limiting Zener diode, e.g., to 5.5V), to establish a voltage V1 (e.g., ≤5.5V), which voltage is passed through a back-flow-prevention diode 48 to produce a DC voltage, Vdc. LSK modulation circuitry 45, including transistors 102 coupled to the charging coil 44, can be controlled by the IPG 10 (via control signal LSK) to transmit data back to the external charger 90 during production of the magnetic field 98 via Load Shift Keying, as is well known.

Vdc is provided to battery management circuitry 84, which may reside on an Application Specific Integrated Circuit (ASIC) along with other circuitry necessary for IPG 10 operation, including current generation circuitry (used to provide specified currents to selected ones of the electrodes 16); telemetry circuitry 43; various measurement and generator circuits; system memory; etc. The front-end charging circuitry 96 and the battery 36 typically comprise off-chip (off-ASIC) components, along with other electronics in the IPG 10, such as the telemetry coil 42; various DC-blocking capacitors coupled to the electrodes 16 (not shown); a microcontroller 100, which can communicate with the ASIC (and the battery management circuitry 84) via a digital bus 88; and other components of lesser relevance here. Microcontroller 100 may comprise in one example Part Number MSP430, manufactured by Texas Instruments, which is described in data sheets at http://www.ti.com/lsds/ti/microcontroller/16-bit_msp430/overview.page?DCMP=MCU_other& HQS=msp430, which is incorporated herein by reference. The ASIC may be as described in U.S. Patent Application Publication 2012/0095529, which is also incorporated herein by reference.

The battery management circuitry 84 in FIG. 2 is comprised of two circuit blocks: charging circuitry 80 for generating a current for charging the battery 36, and load isolation circuitry 82 for controllably connecting or disconnecting the battery 36 from the load 75 that the battery 36 powers during normal operation of the IPG 10. Load 75 can comprise both on-chip (on-ASIC) circuit blocks such as the current generation circuitry and the telemetry circuitry 43 mentioned earlier, and off-chip (off-ASIC) components such as the microcontroller 100.

As depicted, the charging circuitry 80, the load isolation circuitry 82, and the battery 36 generally have a T-shaped topology, with the charging circuitry 80 intervening between front-end charging circuitry 96 (Vdc) and the positive terminal (Vbat) of the battery 36, and with the load isolation circuitry 82 intervening between Vbat and the load 75.

The load isolation circuitry 82 can prohibit the battery 36 (Vbat) from being passed to power the load (Vload) dependent on a number of conditions. For example, if the load 75 is drawing a significantly high current (as indicated by overcurrent detection circuitry 74 via assertion of control signal OI), or if Vbat is too low (as indicated by undervoltage detection circuitry 70 via assertion of control signal UV), or if an external magnetic field signal μ is indicated by a Reed switch 78 (e.g., in an emergency condition warranting presentation by the patient of an external shut-off magnet), the load 75 will be decoupled from Vbat via switches 62 or 64, as assisted by OR gate 76. Discharge circuitry 68 is also provided to intentionally drain the battery 36 if Vbat is too high.

Charging circuitry 80 begins at Vdc, where it splits into two paths connected in parallel between Vdc and Vbat: a trickle charging path, and an active charging path, either of which can be used to provide a charging current (Ibat) to the battery 36 (Vbat).

The trickle charging path is passive, i.e., its operation is not controlled by control signals, and requires no power other than that provided by Vdc to produce a charging current (Itrickle) for the battery 36. As shown, the trickle charging path presents Vdc to a current-limiting resistor 50 and one or more diodes 52, and is used to provide a small charging current, Itrickle, to the battery 36. Using a small trickle charging current is particularly useful when the battery 36 is significantly depleted, i.e., if Vbat is below a threshold Vt1, such as 2.7V for example. Itrickle is usually on the order of ten milliamps.

The active charging path proceeds in FIG. 2 from Vdc to the battery 36 through a current/voltage source 56, which is used to produce charging current Iactive. In the example of FIG. 2, the active charging path also passes through control and protective measures for the battery management circuitry, including a charging current sense resistor 58 used in conjunction with a charging current detector 72, and an overvoltage protection switch 60 used in conjunction with an overvoltage detector 66 to open circuit the active charging path if the battery voltage, Vbat, exceeds a maximum value (such as Vmax=4.2V).

Circuitry for the current/voltage source 56 in the active charging path is shown in FIG. 3A. As its name implies, source 56 can be controlled to provide either a constant current or a constant voltage to the battery 36 during active charging. The source 56 comprises a current mirror comprised of P-channel transistors 104 and 106, which is powered by Vdc and receives a reference current, Iref, provided by reference current generator circuitry 113. Current mirror control transistor 104 mirrors a scaled (M) representation of Iref in current mirror output transistor(s) 106 to produce the active charging current, Iactive=M*Iref.

The reference current generator circuitry 113 used to produce Iref is adjustable via control signals Itrim[2:0], which in turn are used to adjust Iactive. Control signals Itrim are issued by a source controller 86, which receives instructions from the microcontroller 100 by a digital bus 88 (FIG. 2). The source controller 86 likewise issues control signal Ch_en to enable/disable the reference current generator circuitry 113.

The mode in which the source 56 operates to generate a charging current depends on the magnitude of the battery voltage, Vbat, which is known to the microcontroller 100. If the battery 36 is significantly depleted, i.e., Vbat<Vt1 (e.g., 2.7), the microcontroller 100 commands the source controller 86 to disable the source 56 (Ch_en='0') to prevent it from producing Iactive. Thus, the battery 36 in this circumstance can only be charged via the trickle charging path, and only if magnetic field 98 and Vdc are present and sufficient.

If Vbat>Vt1, but below an upper threshold Vt2 described further below (i.e., if Vt1<Vbat<Vt2), the source 56 operates in a constant current mode. In this mode, the source 56 is enabled (Ch_en='1'), allowing Iactive to flow in accordance with a value represented by the Itrim control signals. When source 56 operates in constant current mode, Iactive is generally on the order of 50 milliamps.

If Vbat>Vt2 (e.g., 4.0 V), the source 56 operates in a constant voltage mode. Crossing of the Vt2 threshold and switching of charging modes is affected via Vbat measurement circuitry 111, which controls amplifier 112 to start turning off transistor 114 in the active charging path. The value of Vt2 is set by the Vtrim control signals. Once in constant voltage charging mode, Iactive thus begins to fall off exponentially, until Vbat reaches a maximum value, Vmax (e.g., 4.2V), at which point the microcontroller 100 will consider charging of the battery 36 to be complete. FIG. 3B generally illustrates operation of the charging circuitry 80 to produce the charging current (Ibat) received by the battery 36 as a function of time during a charging session, including the trickle, constant current, and constant voltage modes.

The battery management circuitry 84 of FIG. 2 provides additional safeguards, such as diode(s) 54 connected between the trickle and active charging paths to prevent leakage of the battery 36 through the overvoltage switch 60.

Referring again to FIG. 2, the microcontroller 100 in the IPG 10 includes an shutdown register 115, in which is stored a future time or time interval from beginning of use of the IPG 10 (tSD) at which the IPG will cease therapeutic operations (although non-therapeutic operations such as telemetry may still function if possible), and will thus no longer provide stimulation therapy to the patient. tSD in the shutdown register 115 is typically set by the IPG manufacturer, and may comprise 12 years in one example. Once tSD is reached, the IPG 10 will need to be explanted from the patient, and a new IPG implanted. tSD may be populated in the IPG, or the 12-year time interval may start running, under manufacturer or implanting clinician control for example.

tSD serves important purposes. First, tSD may represent a time after which the manufacturer believes the IPG 10 might fail or begin working unreliably or unsafely, perhaps as determined via reliability testing at the manufacturer. Second, tSD sets a date after which the manufacturer's responsibility or liability for the IPG 10 is limited or suspended. For example, the manufacturer may provide a warranty and support regarding the IPG 10 and supporting external components which expires once tSD has passed. Thus, tSD provides certainty to the manufacturer as to its obligations vis-à-vis the IPG and the patient.

Third, tSD is used to warn the patient or clinician in advance that IPG 10 operation will soon be suspended. In this regard, the IPG 10 determines an early replacement indicator from tSD, which may be timed to occur (tSDi) at a set time period (tGRACE) before tSD occurs (i.e., tSDi=tSD−tGRACE). tSDi may be stored in its own register 117 as shown. When tSDi arrives, an indication is provided to a patient or clinician external device via telemetry from the IPG 10 using telemetry coil 42 and its associated telemetry circuitry 43. The IPG 10 may attempt to initiate such communications, or the IPG 10 may hold the tSDi indication in a manner flagging it as priority data to be sent to the external device once the external device initiates a communication session with the IPG 10. Once communicated to the external device, the tSDi indication can for example be viewed on a display of the external device, informing the patient that IPG operation will soon be suspended, and perhaps also informing the patient of the particular date or time that tSD will occur. This early warning allows the patient to plan to contact his clinician or the manufacturer to discuss explanation of the IPG 10, and replacement with a fresh IPG.

However, the inventors consider it unfortunate that tSD (and by extension, its earlier indicator tSDi) comprises a fixed time period set by the manufacture at the outset of use of the device. The inventors recognize that in reality the time at which IPG 10 would reach its end of its life will be determined at least in part by how strenuously the IPG 10 is used by each patient. For example, if an IPG provides relatively low stimulation therapy to a patient, that patient's IPG may still be perfectly functional and safe even after tSD has passed. Such a patient might wish to continue to use the IPG 10 after this time (even if not warranted or supported by the manufacturer) to delay explantation surgery as long as possible. Moreover, the manufacturer may be willing to extend warranty and support to such a patient for at least some period beyond tSD. On the other hand, another patient requiring more strenuous stimulation therapy may exhaust the life of his IPG before tSD expires. This presents a problem for both the patient and the manufacturer: the patient may be upset regarding the IPG's performance, having expected it to last at least until tSD, and must undergo explantation earlier than expected; and the manufacturer may need to continue to warrant and support the IPG, even though the IPG was not faulty, but was nonetheless used (perhaps unusually) strenuously.

SUMMARY

Circuitry for a medical device is disclosed, comprising: a rechargeable battery; control circuitry configured to configured to implement an algorithm, wherein the algorithm is configured to: estimate a first capacity of the battery, and forecast and/or determine an end of life of the medical device using at least the estimated first capacity of the battery.

The algorithm may be further configured to store previously-estimated battery capacities, and the algorithm may forecast and/or determine the end of life using the estimated first capacity and the previously estimated capacities. The first and previously estimated battery capacities may each be associated with a time, and wherein the algorithm forecasts and/or determines and end of life by deriving a function of battery capacity versus time.

The algorithm forecasts and/or determines the end of life in accordance with a first capacity threshold, and may be configured to forecast and/or determine an early indicator of the end of life. The early indicator may comprises a set time before the forecasted end of life, or the algorithm may forecast and/or determine the early indicator in accordance with a second capacity threshold. The algorithm may be further configured to store the forecasted and/or determined early indicator for transmission to an external device.

The algorithm may suspend therapeutic operation of the medical device when the end of life is determined, or may use the forecasted end of life to extend therapeutic operation of the medical device beyond a shutdown time.

The control circuitry may further comprises a memory configured to store at least one parameter having an effect on a capacity of the rechargeable battery, wherein the at least one parameter is selected from a group consisting of one or more parameters relevant to: previous charging of the battery, previous use of the medical device to provide therapy, and the age of the battery; in which the algorithm is configured to estimate the first capacity of the battery using the at least one parameter. The at least one parameter may be stored as a function of time in the memory, or stored as a present value for use by the algorithm. The at least one parameter may also comprises a value computed from at least one other parameter measured during previous charging of the battery or previous use of the medical device.

Parameters relevant to previous charging of the rechargeable battery may comprise a number of previous charging session, a voltage of the battery at the start of a previous charging session, a voltage of the battery at the end of a previous charging session, a duration of a previous charging session, a charge provided to the battery during a previous charging session, a discharge depth comprising a difference between a voltage of the battery at the start and finish of a previous charging session, and a battery charging current provided to the battery during a previous charging session.

Parameters relevant to previous use of the medical device to provide therapy may comprise a voltage of the rechargeable battery during a previous use, a load current drawn from the battery during a previous use, a power drawn from the battery during a previous use, a duration a use, and a charge drawn from the battery during a previous use.

The circuitry may further comprises a battery capacity database, in which the battery capacity database associates the at least one parameter with a change in the capacity of the battery, wherein the algorithm compares the at least one parameter to a change in the capacity in the battery capacity database to determine the first capacity of the battery. The memory may further comprises a weight or priority of each at least one parameter, in which the algorithm is configured to determine the first capacity of the battery by using the weigh or priority or both the weight and priority of the at least one parameter.

Also disclosed is a method for operating a medical device having a rechargeable battery, comprising: estimating a first capacity of the rechargeable battery, and forecasting and/or determining an end of life of the medical device using at least the estimated first capacity of the battery. The disclosed method may use aspects of the circuitry as described above.

Further circuitry for a medical device is also disclosed, comprising: a rechargeable battery; a first register configured to store a shutdown time at which therapeutic operation of the medical device will be suspended; control circuitry configured to configured to implement an algorithm, wherein the algorithm is configured to: determine an end of life of the medical device using at least a first estimated capacity of the battery; and suspend therapeutic operation of the medical device even if the shutdown time has not been reached. The algorithm may be further configured to resume therapeutic operation of the medical device upon receipt of an override. The algorithm may be further configured to forecast an end of life of the medical device using at least a second estimated capacity of the battery; determine that the shutdown time has been reached; continue therapeutic operation of the medical device if the forecasted end of life is greater than the shutdown time; and suspend therapeutic operation of the medical device if the determined end of life is not greater than the shutdown time. The algorithm may be configured to continue therapeutic operation of the medical device by adjusting the shutdown time to a later time in the first register, which later time may be between the shutdown time and the forecasted end of life or which may be of a fixed duration.

Further circuitry for a medical device is also disclosed, comprising: a rechargeable battery; a first register configured to store a shutdown time at which therapeutic operation of the medical device will be suspended; control circuitry configured to configured to implement an algorithm, in which the algorithm is configured to: forecast an end of life of the medical device using at least a first estimated capacity of the battery; determine that the shutdown time has been reached; continue therapeutic operation of the medical device if the forecasted end of life is greater than the shutdown time; and suspend therapeutic operation of the medical device if the determined end of life is not greater than the shutdown time. The algorithm may be configured to continue therapeutic operation of the medical device by adjusting the shutdown time to a later time in the first register, which later time may be between the shutdown time and the forecasted end of life, or which may be of a fixed duration.

BRIEF DESCRIPTION OF THE DRAWINGS

FIG. 3A shows circuitry for a current/voltage source in the active current path, while FIG. 3B shows a graph of the battery charging current provided by both the trickle and active charging paths as a function of time, in accordance with the prior art.

FIG. 5A shows a capacity-relevant parameter log, FIG. 5B shows present capacity-relevant parameters determined from the log, and FIG. 5C shows a battery capacity database, which are used in accordance with the EOL algorithm, in accordance with an aspect of the invention.

FIGS. 6A-6E show initial operation of the EOL algorithm, in accordance with an aspect of the invention.

DETAILED DESCRIPTION

Figure 1A:
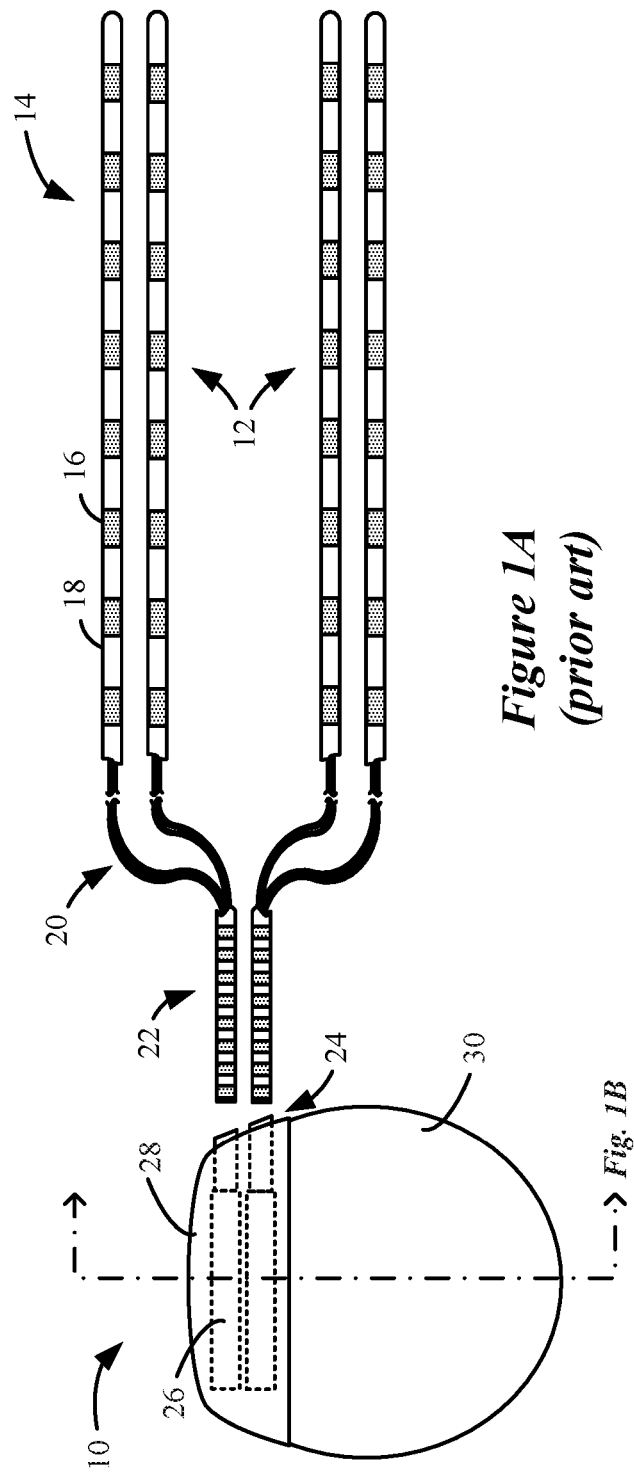
FIGS. 1A and 1B show an implantable pulse generator (IPG) with a rechargeable battery in plan and cross sectional views, in accordance with the prior art.
Figure 1B:
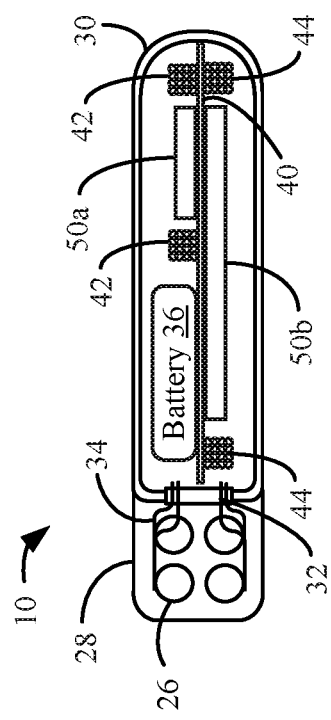

Many events can occur which could cause an Implantable Medical Device (IMD) such as an IPG to reach its end of life at a time tEOL. The circuitry could fail, either as a result of defects, or because the circuitry has simply worn out and is no longer operating in accordance with its specifications. Mechanical defects or wear out can also cause the IMD to fail, such as a breech in the IMD's hermetic case 30, mechanical damage to the electrical components in the case 30 and in the header 28, etc.

Additionally, the end of life of an IMD may result from wear out of its rechargeable battery. The inventors consider rechargeable battery wear out to be a predominant factor in determining the life of a rechargeable battery IMD. Battery wear out—more specifically loss of battery capacity—may be of greater significance than other electrical or mechanical failure modes. Although random electrical and mechanical defects can occur in an IMD, circuitry and mechanics in the IMD should otherwise last a lifetime before they are worn. Loss of battery capacity by contrast will occur in any rechargeable-battery IMD, and such wearing of the battery will often cause the IMD to stop working satisfactorily long before electrical or mechanical wear out would do so.

The inventors are aware that certain parameters can affect the capacity of the rechargeable battery over the lifetime of an IMD, including battery calendar age (A), and various parameters pertaining to stresses imparted to the rechargeable battery. Such parameters can relate to battery charging, such as the number of times the battery has been recharged (Nc); the charging current used to recharge the battery (Ibat); how long it takes to recharge the battery (Tc), which in conjunction with the charging current determines the total charge (Cc) the battery has received (Cc=Ibat*Tc); and the discharge depth indicating the difference in the battery voltage from the start to the finish of a charging session ($\Delta$Vbat). Such parameters can also relate to use of the battery to provide power to the IMD, such as the current (Iload) or charge (Cu=Iload*Tu, where Tu equals the time of use) drawn from the battery by the load 75 during regular operational periods in which battery charging may not be occurring.

These parameters tend to reduce the capacity of the battery over time as they contribute to chemical and physical changes in the rechargeable battery. As battery capacity decreases over time, the rechargeable battery will eventually wear to a point where it can no longer be charged to operate the IMD for a significant time. In this regard, considering when the rechargeable battery has reached its end of life may be subject to interpretation. For example, if it takes an hour to recharge the battery, which then enables the IMD to provide therapy for only an hour, most would consider the rechargeable battery to have reached the end of its life as a practical matter, even though technically the battery can still be used and hasn't suffered a catastrophic failure. In short, the end of life of a rechargeable battery (at time tEOL) is largely a qualitative judgment. While the shutdown time tSD used in the prior art may desire to approximate the tEOL, the two are not the same, as tSD does not consider actual stresses that rechargeable battery will endure during use, which can vary from patient to patient. As implied in the Background, tEOL for a light-use IMD patient may be well beyond tSD, and tEOL for a strenuous-use IMD patient may be well before tSD. In neither case does tSD comprise an actual quantitative determination that the rechargeable battery IMD has actually reached its end of life, but is instead, at best, a statistical value derived from reliability testing, which as just noted may not fit all realistic IPG use situations.

The inability of the prior art to quantitatively determine tEOL for a rechargeable battery IMD is problematic because a rechargeable battery of reduced capacity will be more easily depleted to unsuitably low levels, or will do so more quickly that when the battery 36 was new. If Vbat is severely depleted, i.e., if Vbat<2.0V for example, it may be difficult to recover (recharge) the battery 36. This is explained in further detail in the above-referenced 2015/0196768 Publication, which may be used in conjunction with the disclosed technique. In short, without a quantitative measure of tEOL, the risk of such battery depletion is increased. This is particularly true for strenuous-use IMD patients, who are otherwise permitted by the prior art to use their implants prior to the expiration of tSD, when in reality they have exhausted their IMDs and should have them explanted.

In contrast to rechargeable battery IMDs, tEOL of a non-rechargeable battery IMD is easier to determine, and can simply comprise a battery voltage threshold, e.g., Vbat (EOL), below which the non-rechargeable battery can no longer reliably operate the circuitry in the IMD. Moreover, tEOL can also be more easily forecasted for a non-rechargeable battery IMD. For example, the IMD can track Vbat as it decreases over its life, and can extrapolate as to when Vbat is likely to reach Vbat(EOL), thus providing a quantitative means of forecasting tEOL. Moreover, the ability to easily quantify tEOL in non-rechargeable IMDs allows for warning the patient in advance that tEOL is impending, such as by the issuance of an early replacement indicator (EOLi), similar to the manner in which advanced notice of shutdown at tSD is provided to the rechargeable battery IMD patient by tSDi. The time at which tEOLi may issue for a non-rechargeable battery IPG can, like tSDi, be set in accordance with fixed a grace period referenced to tEOL (i.e., tEOLi=tEOL–tGRACE), or may also occur when the battery voltage passes a threshold Vbat(EOLi) that is slightly higher than Vbat(EOL). See, e.g., U.S. Patent Application Publication 2015/0100108. Of course, forecasting tEOL using Vbat as a function of time is not possible in a rechargeable battery IMD: Vbat does not continually decrease over the life of a rechargeable battery IMD, but instead oscillates as the battery is continually used and recharged.

The inventors have determined that it is desirable to quantitatively determine when tEOLi and tEOL have been reached for a rechargeable battery in an IMD, and similarly to quantitatively forecast when tEOLi and tEOL might issue in the future. These determinations and forecasts for tEOLi and tEOL occur in accordance with one or more of the capacity-relevant parameters noted above, including parameters relevant to battery charging (e.g., Nc; Ibat; Tc; Cc; $\Delta$Vbat), battery use (e.g., Iload), and/or battery age (A). Specifically, an algorithm operable in the IMD consults such parameters as stored over the history of the operation of the IMD in a parameter log, and determines and forecasts tEOLi and tEOL accordingly, as will be explained below.

Quantitatively determining and forecasting tEOLi and tEOL is significant in the context of a rechargeable battery IMD, and to the inventors' knowledge is novel. Unlike the prior art discussed earlier in which tSDi and tSD for a rechargeable battery IMD are merely predetermined by the manufacturer at the outset of the IPG's life, the disclosed technique instead considers parameters in the IMD reflective of the stresses on the rechargeable battery's capacity, which as noted earlier can drive tEOL, and hence its associated tEOLi. Such parameters can for example distinguish light or strenuous use of the rechargeable battery in the IMD, which as noted above can vary from patient to patient, thus allowing tEOLi and tEOL to be determined or forecasted for each IMD and each patient based on such use. Thus, light use of the IMD by a particular patient will result in an increased values for tEOLi and tEOL, while heavy use by a particular patient will result in a decreased values for tEOLi and tEOL.

In short, the disclosed technique provides a quantitative and realistic way of determining and forecasting the end of life of the rechargeable battery IMD, aiding both the patient and the manufacturer. The manufacturer may for example sell the IMD with conditional warranty and support obligations contingent on tEOL as forecasted or determined. Thus, the manufacturer's obligation to a strenuous-use IMD patient may expire or be limited more quickly than traditional preset times (e.g., tSD) would warrant (e.g., <12 years). Conversely, the manufacturer may allow a light-use patient to continue operating her IMD beyond tSD, and/or may allow its warranty and support obligations to be extended beyond tSD if tEOL for a light-use IMD patient is determined or is forecasted to occur later (e.g., >12 years). Thus, the IMD may not simply stop operating upon expiration of tSD, as discussed further below.

Figure 2:
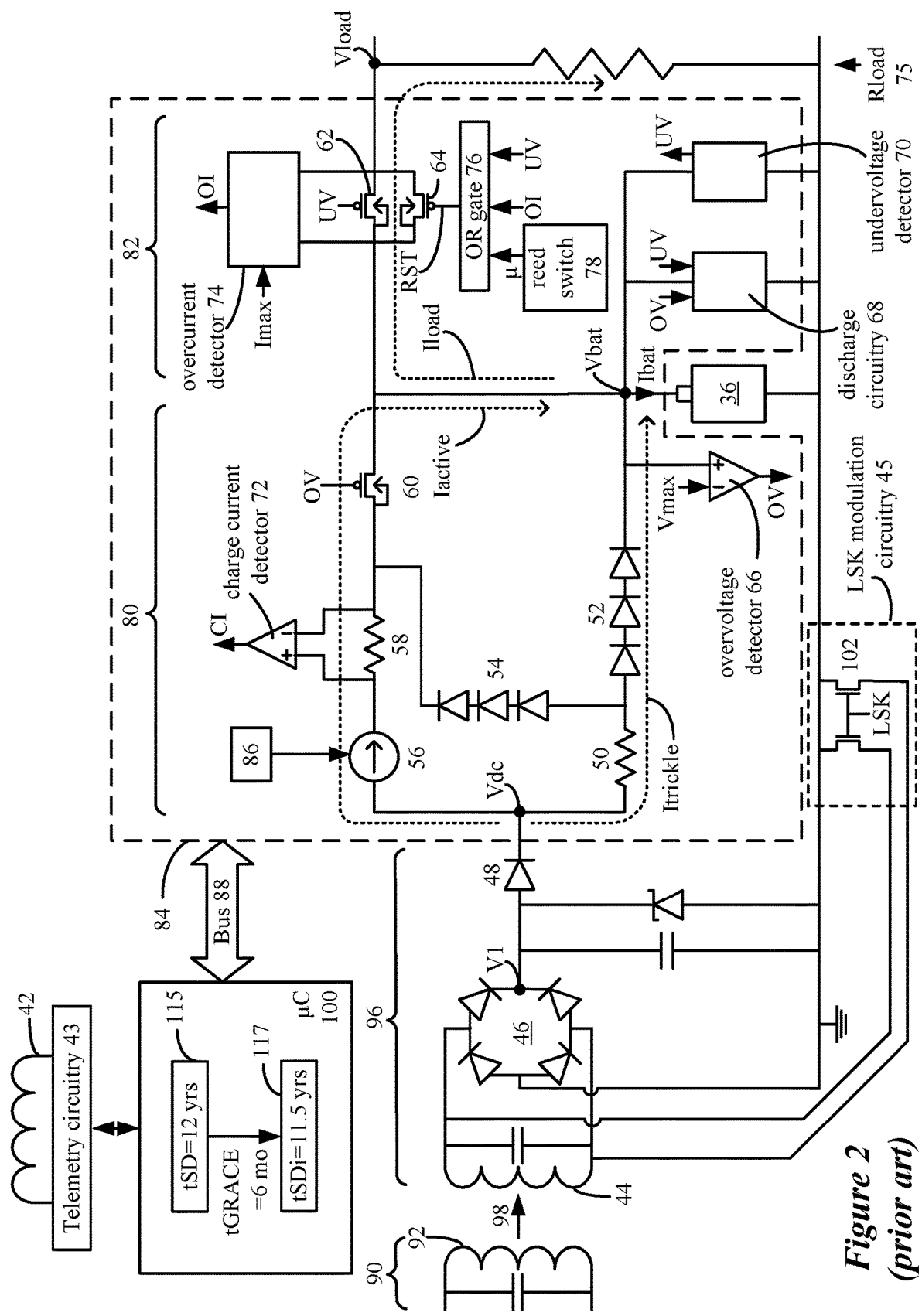
FIG. 2 shows battery management circuitry for the rechargeable battery IPG including both trickle and active charging paths, in accordance with the prior art.
Figures 3A, 3B:
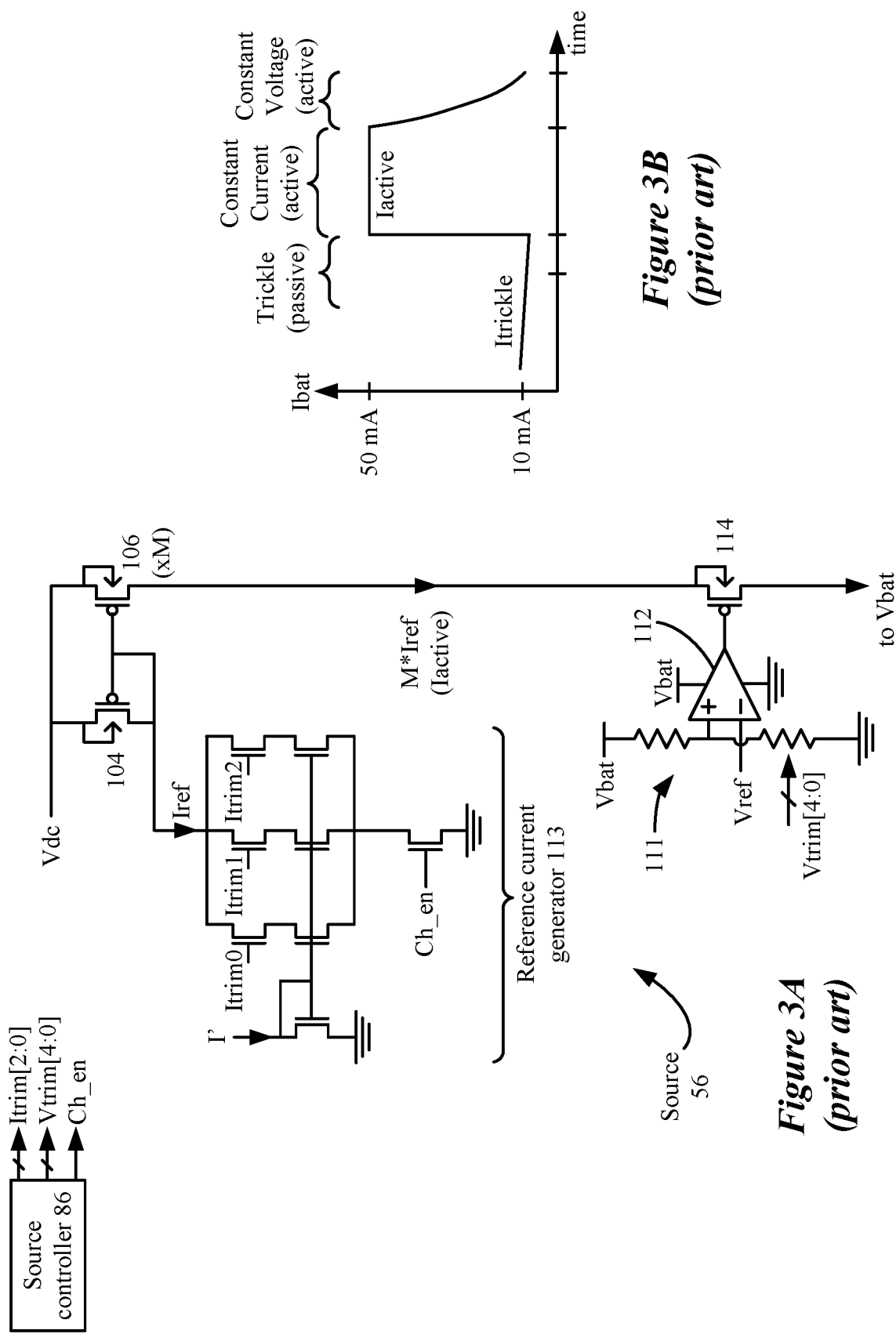
Figure 4:
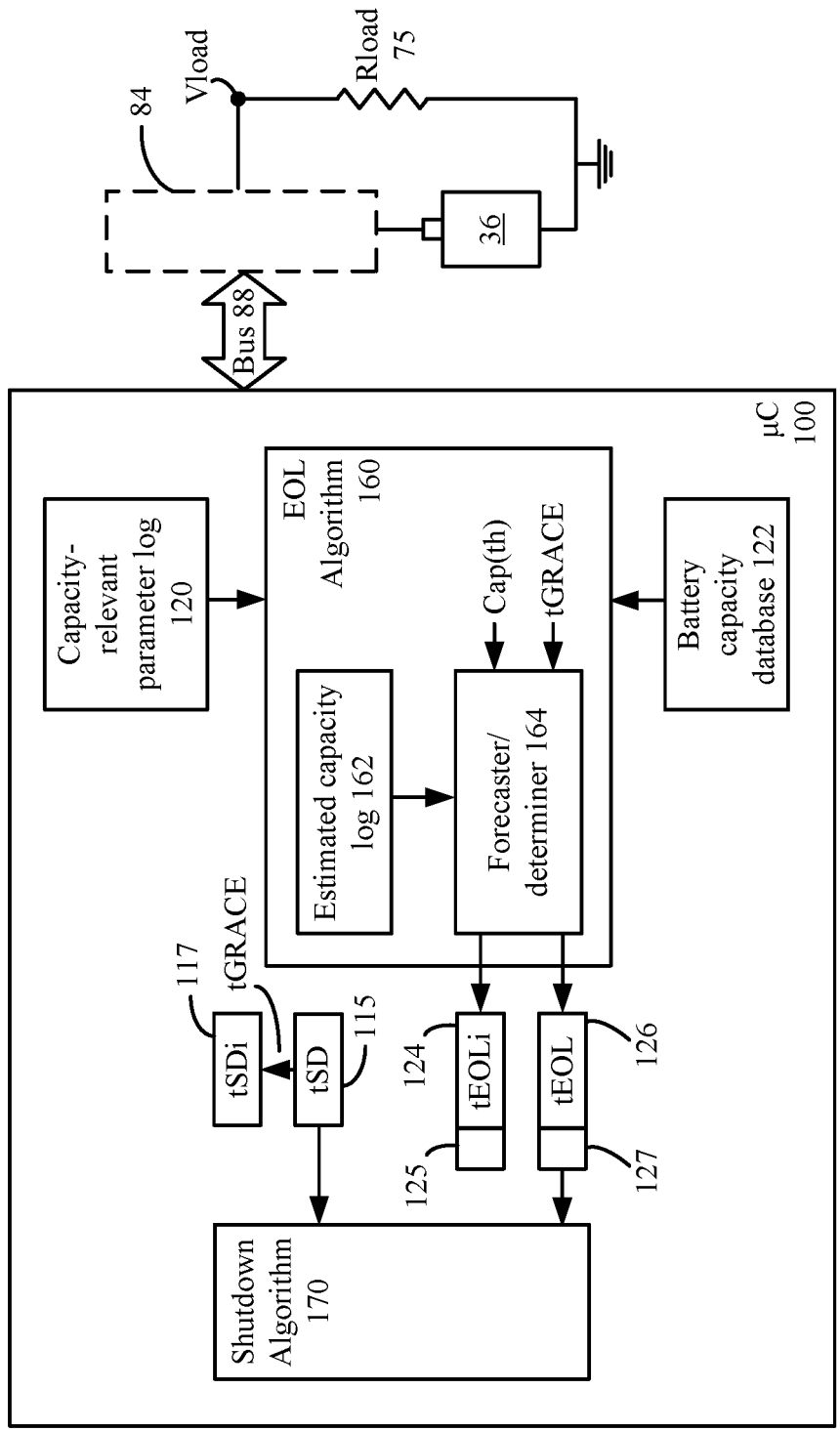
FIG. 4 shows improved circuitry for a rechargeable battery IPG including an algorithm used to forecast and determine tEOLi and tEOL in accordance with logged historical parameters relevant to rechargeable battery capacity, in accordance with an aspect of the invention.

FIG. 4 shows improved circuitry for an implantable medical device such as an IMD 10 having a rechargeable battery 36 which allows for tEOLi and tEOL determination and forecasting. Many of the components are unchanged from the prior art as shown in FIG. 2, and are thus not described again for simplicity.

The microcontroller 100 has been programmed to implement an EOL algorithm 160. Input to the algorithm 160 are two data sets: a capacity-relevant parameter log 120, and a battery capacity database 122, which are shown in detail in FIGS. 5A-5C. Stated simply, the capacity-relevant parameter log 120 contains historical parameters such as those discussed above that have an impact on battery capacity, including data regarding past charging and use of the IMD 10 and its age. The battery capacity database 122 comprises data correlating the parameters to battery capacity. This database 122 is preferably programmed by the manufacturer based on its understanding of the relevance of the parameters to the particular rechargeable battery 36 at hand.

Thus, the EOL algorithm 160 reviews historical parameters relevant to battery capacity in the log 120, and reviews such parameters in light of the correlations in the database 122, to determine and forecast tEOLi and tEOL. As shown, additional registers 124 and 126 are provided to store tEOLi and tEOL as forecasted or determined. Indicator bits 125 and 127, which may be associated with the registers 124 and 126, can comprise single bits indicating whether tEOLi and tEOL have already been determined—that is, if these times have already been reached.

The shutdown register 115, including its present shutdown time tSD, can also be provided in the IPG 10, as occurred in the prior art. However, as discussed further below, while tSD can still operate to shut down operation of the IMD 10, it doesn't necessarily do so, or it can be adjusted to be commensurate with tEOL as forecasted.

One example of the capacity-relevant parameter log 120 is shown in FIG. 5A. Note that some or all of the data in the log 120 may already be stored during normal operation of the IMD 10, and thus log 120 merely shows the collection of such data in a convenient form. For ease of viewing, the capacity-relevant parameter log 120 has been split into three sections 120*c*, 120*u*, and 120*a*.

Section 120*c* contains historical parameters procured or computed during previous charging sessions, including the number of the charging session (Nc); the voltages of the battery 36 at the start and finish of the charging session (Vbat(i), Vbat(f)), from which the discharge depth (ΔVbat) can be computed; and the charging current, Ibat. Note that Ibat preferably comprises a measurement of the actual current provided by the source 56 in the active charging path, as opposed to the Iactive value to which the source 56 was programmed (by the Itrim control signals). This is preferable, because programming the source 56 (FIG. 2) to provide a particular Iactive does not guarantee that such current was actually provided to the battery 36. This is particularly true if the coupling between the external charger 90 and the IMD 10 is poor, providing a Vdc to the source 56 that is too low to produce the programmed current. The actual Ibat in the log 120 may be measured using by sensing a voltage drop across charging current sense resistor 58 using charging current detector 72, which produces an analog signal CI that can be digitized (FIG. 2).

Note that Ibat in the capacity-relevant parameter log 120 contains no data concerning the trickle charging path (Itrickle) during the relevant charging session. As Itrickle is generally low compared to Iactive, its contribution as a parameter relevant to battery capacity and hence tEOLi/ tEOL may be insignificant, and thus ignored. This is fortunate, because Itrickle may be difficult to accurately measure, as Vbat is low, and the IMD 10 circuitry thus unreliable, when significant trickle charging is occurring.

Also shown in section 120*c* is the duration of the charging session (Tc). This may be determined using the IMD's internal clock, as reflected in the timestamp values that are optionally provided in the log 120. From the charging time Tc, a total charge (Cc) provided to the battery during the charging session may be computed (Ibat*Tc).

Section 120*u* shows parameters relevant to battery capacity during regular use of the IMD 10, for example, to provide therapy to the patient. As noted above, the power drawn by the IMD 10 (e.g., Iload) affects battery capacity, and so Iload is included in 120*u*. Although not shown, the battery voltage Vbat could also be provided in 120*u*, which would provide a truer indication of power draw (P=I*V), which may also be included as a parameter in 120*u*. Use durations (Tu) are also provided, from which a total charge (Cu) can be determined (Iload*Tu). Note that Iload is a dynamic parameter when the IMD 10 operates, and will be significantly higher during those time periods when the IMD 10 is actually providing pulses to the electrodes 16. As such, the frequency, duration, and intensity of such pulses will affect (or largely determine) Iload and Cu, which may represent a scaled or average value. See, e.g., U.S. Pat. No. 9,433,796. Iload can also be measured directly, using the technique disclosed in U.S. Pat. No. 9,364,673. Although the timestamps in sections 120*c* and 120*u* suggest for simplicity that charging and use do not overlap in time (note the interleaved timestamps, tx), this is not strictly necessary, as the IMD 10 can generally continue to be used during a charging session.

Section 120*a* merely shows the IMD's age, as reflected by the current timestamp. Note that the some of the parameters in log 120 that originate in battery management circuitry 84 (e.g., Ibat, Iload) can be communicated to the microprocessor 100 via the bus 88 for storage in the log 120.

The particular structure of capacity-relevant parameter log 120 can vary, and need not comprise a unified single structure or file used by the EOL algorithm 160. Particularly if some of the parameters are already logged in the IMD 10 for some other reason, the parameters may reside in different data structures in the IMD, which are simply queried by the algorithm 160. The algorithm 160 may additional include the ability to compute relevant parameters (e.g., charge Cc, which equals Ibat*Tc), and so the log 120 need not precompute such values for the algorithm 160's convenience.

Note that the illustrated parameters comprising log 120 are subject to manufacturer preferences, and perhaps even manufacturer experience with the wear out of the particular rechargeable battery 36 used in the IMD. Thus, a manufacturer may consider some of the parameters illustrated in FIG. 5A to be irrelevant (or of only minor relevance) to battery capacity, and so may not be included in the log 120. Another manufacturer may consider additional parameters not shown to be more relevant to battery capacity, and so may include such additional parameters. In short, the parameters included in the capacity-relevant parameter log 120 as illustrated in FIG. 5A should be understood as only one example of the parameters useful for tEOLi and tEOL forecasting and determination.

As discussed in detail later, the EOL algorithm 160 will consult the parameters in the log 120 to adjust tEOLi and tEOL from time to time. FIG. 5B shows a manner in which the data in the log 120 may be summarized for easier use by the algorithm 160 in the form of present capacity-relevant parameters 120', which summarizes the parameters for use by the algorithm at the present time. For example, the total charge imparted to the battery 36 during charging over the life of the IMD, Cc(tot), is provided, which comprises a sum of the charge values Cc from section 120*c* of the log 120. As shown in FIG. 5B, this summed charge is currently represented by value Cc(tot)2, which would grow over time. The total charge expended during use of the IMD, Cu(tot) is similarly provided, which is currently represented by value Cu(tot)2. Also provided in present parameters 120' is the total number of times the IMD has been charged, Nc, as represented currently by Nc4, which would comprise the last value for Nc in section 120*c* of the log 120. Average discharge depth, ΔVbat(avg), and average charging and use currents, Ibat(avg) and Iload(avg), are also provided by averaging the individual values in section 120*c*.

Present capacity-relevant parameter Z in log 120' comprises a ratio of the charge expended during use (Cu(tot)) and the charge imparted to the battery during charging (Cc(tot)). This parameter is relevant, and should ideally equal one, because the charge input to the battery and output from the battery should theoretically be the same absent a problem. Of course, the uracy of this ratio depends on how accurately the total charges can be calculated. Nonetheless, a baseline value of Z for a properly operating IMD 10 with good battery capacity can still be established even if the total charges are imperfectly measured. If the value for Z decreases over time, this suggests that an increasing amount of charge imparted to the battery during charging is not being used by the circuitry in the IMD, and hence that a battery capacity problem may exist such as leakage in the rechargeable battery 36.

Just as the parameters included in the log 120 are subject to manufacturer preferences and experiences, so too is the data included in present parameter log 120', and the manner in which such data is digested from the log 120. To cite some simple examples, the manufacturer may consider small discharge depths (ΔVbat) to be irrelevant to battery capacity and operation of the EOL algorithm 160, and so may exclude values smaller than a threshold from the average in 120'. Or, the manufacturer may wish to include as a present parameter in 120' the percentage of the time that the discharge depth has historically been above this threshold.

Present parameters 120' may also not necessarily reflect data occurring over the entire history of the log. For example, Ibat(avg), Iload(avg), and ratio Z may be more relevant when determined from more-recent data in the log 120, and thus may be computed using only data in the log occurring over a recent time period, such as one month. Using only a recent portion of the log 120 may be particularly useful if changes to the operation of the IMD 10 are made that would impact battery capacity. For example, in the above-referenced 2015/0196764 Publication, which may be used in conjunction with the disclosed technique, it is taught that the charging current Ibat can be adjusted (e.g., reduced) over time to decrease the rate at which the battery capacity is decreasing. Should this occur, it may be warranted to assess only capacity-relevant parameters in the log 120 that have occurred since such adjustment so that the tEOLi and tEOL forecasts and determinations are not skewed by old data that is no longer representative of the current stresses on the IMD and rechargeable battery 36.

The parameters illustrated in FIG. 5B provide merely one example useful to illustrating the disclosed technique. Present capacity-relevant parameters 120' may comprise a portion of the log 120, or be separate. Also, the present capacity-relevant parameters 120' may be automatically updated pursuant to a schedule, or computed or updated once the EOL algorithm 160 runs.

An example of the battery capacity database 122 is shown in FIG. 5C. As noted earlier, the battery capacity database 122 comprises data correlating the parameters in the log 120 (or preferably the parameters as digested in log 120') to battery capacity. As shown, the database 122 depicts how particular values for the parameters affects battery capacity. For example, if the total charge provided to the battery during charging comprises a value of Cc(tot)2 (or a value between Cc(tot)2 and Cc(tot)3), database 122 reflects that battery capacity is reduced by 2%. Note that the effect of battery capacity could also be reflected in database 122 using values other than percentages, although percentages are used herein for easy illustration.

As noted, the data in database 122 is preferably determined by the IMD or battery manufacturer based on their understanding of the effect of each of the parameters on battery capacity. For example, in determining an appropriate percentage adjustment for parameter Cc(tot), the manufacturer may experimentally determine or measure the battery capacity once Cc(tot)1, Cc(tot)2, etc. have been reached, and set the percentages in the database 122 accordingly.

As shown for simplicity in FIG. 5C, the relationship between the parameter values and the percentages in FIG. 5C are reflective of the effect of just that parameter on battery capacity, absent consideration of other parameters. Alternatively, although not shown, more complicated multi-parameter relationships may be reflected. For example, database 122 may reflect a percentage dependent on two or more parameters: e.g., if Cc(tot)>A, but Iload(avg)<B, then the percentage is C %; or if ΔVbat(avg)*Ibat(avg)=P(avg)>X, then the percentage is Y, etc.

Note that most of the parameters in battery capacity database 122 reflect that battery capacity decreases (hence the negative percentages) as the values for the parameters increase. However, this is not always the case, such as for ratio Z discussed above. Moreover, while all of the parameters are shown to result in a reduction of battery capacity, this might not always be the case, as some parameters (particularly if different battery chemistries are used, or given how the various parameters are mathematically processed) might result in an increased capacity over time (a positive percentage).

Battery capacity database 122 additionally may include data regarding the weight of the parameters, or a priority in which such parameters should be applied by the EOL algorithm 160 when determining or forecasting tEOLi and tEOL. For example, it is seen that the manufacturer considers total charge during charging (Cc(tot)) to be the parameter having the most significant impact on battery capacity. Thus, this parameter is provided a weight of '1' (suggesting it will be fully considered by the algorithm 160 without scaling), and is accorded the highest priority. By contrast, the average discharge depth (ΔVbat(avg)) is deemed to be less significant, and thus carries a weight of 0.5 and is fourth highest in priority. Again, these weights and priorities in database 122 are subject to manufacturer preferences and experience.

Figure 6A:
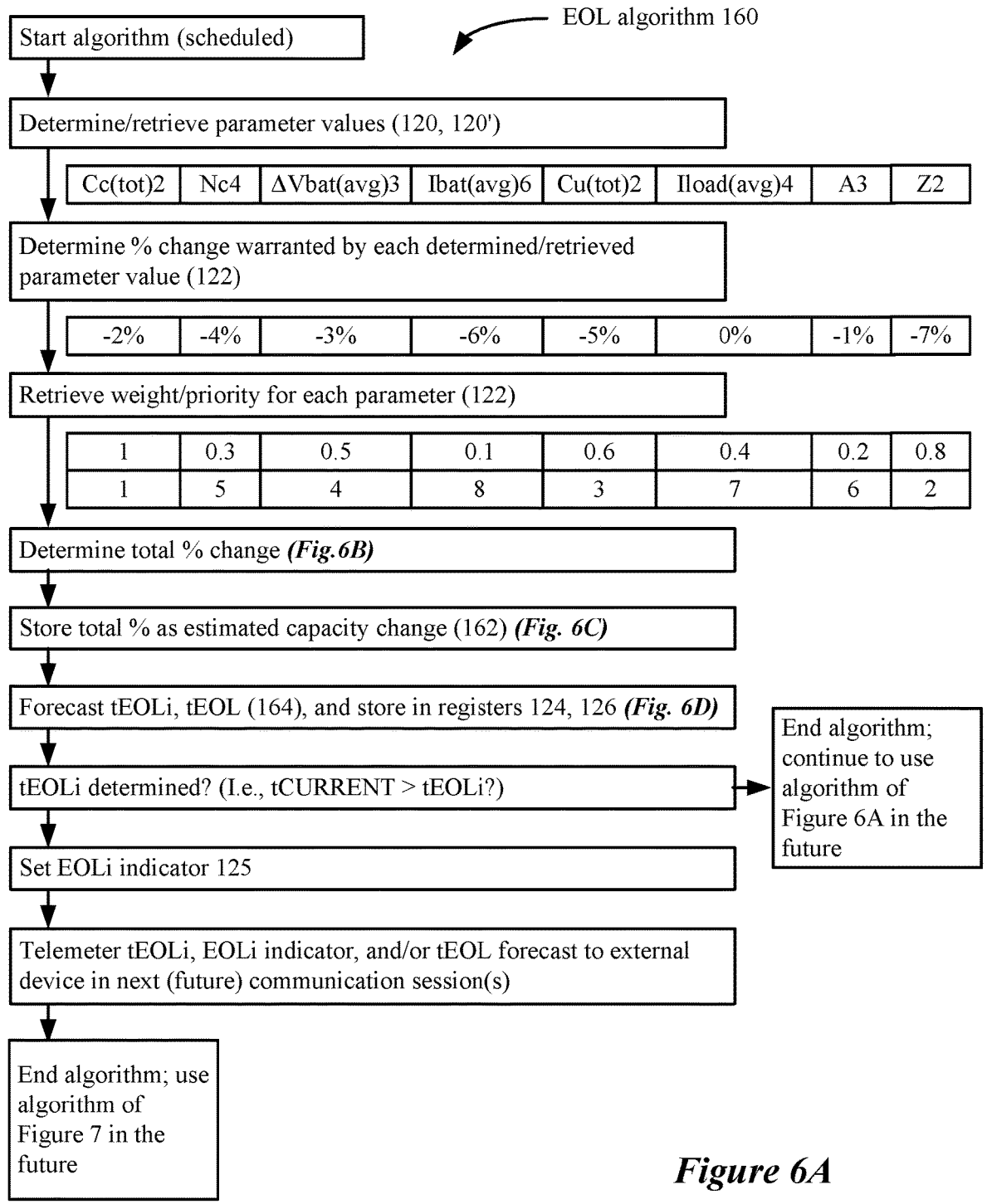
Figure 7:
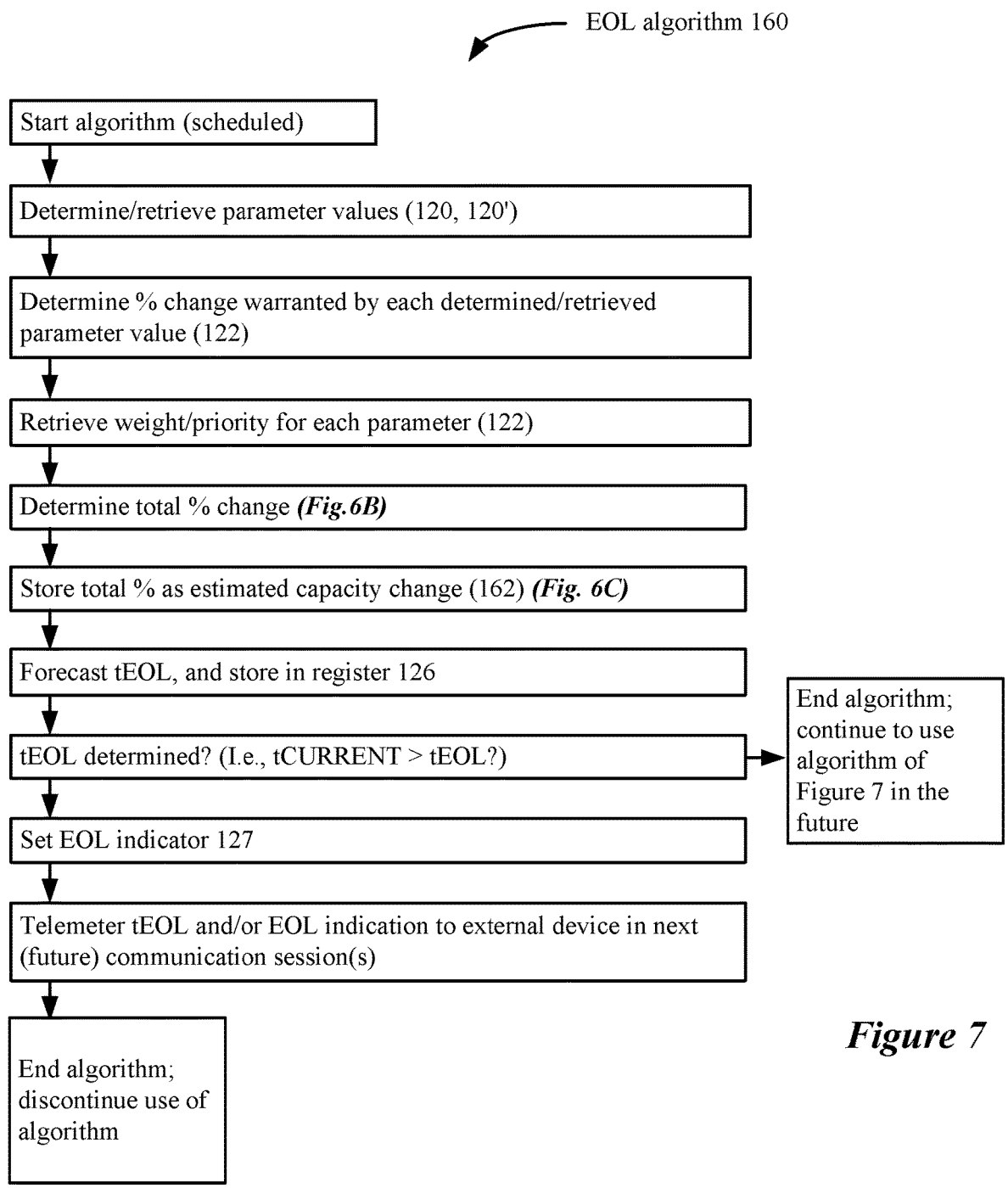
FIG. 7 shows later operation of the EOL algorithm, in accordance with an aspect of the invention.

FIG. 6A illustrates the EOL algorithm 160 in one example. This portion of the algorithm 160 is used initially, before tEOLi (and hence tEOL, which occurs later) is determined. That is, tEOLi has not yet been reached, and EOLi indicator bit 125 (and hence EOL indicator bit 127) has not yet been set in a previous run of the algorithm 160. Thus, the portion of algorithm 160 illustrated in FIG. 6A seeks to forecast (or update the forecast of) tEOLi and tEOL, and to assess whether tEOLi has been determined and thus that EOLi indication bit 125 can be set. FIG. 7, discussed later, illustrates later operation of the EOL algorithm 160 once tEOLi has been determined (indicator bit 125 set), but tEOL has not. Thus, the portion of algorithm 160 illustrated in FIG. 7 seeks to forecast (or update the forecast of) tEOL, and to assess whether tEOL has been determined and thus that EOL indication bit 127 can be set. After both tEOLi and tEOL have been determined (both indicator bits 125 and 127 have been set), there is no further need to run algorithm 160, and thus the microcontroller 100 will preferably suspend operation of the algorithm 160 in any form at that time. Note that the EOL algorithm 160 in FIGS. 6A and 7 do not consider the preset shutdown time (tSD) or its early indicator (tSDi) that may still be included in the IMD 10 (in registers 115 and 117; FIG. 4). Discussion of the relevance of use of the shutdown time tSD in the context of the IMD is discussed with reference to shutdown algorithm 170 of FIG. 8.

As shown, the EOL algorithm 160 can be designed to run automatically on a schedule, with a periodicity long enough to gather a significant amount of new capacity-relevant parameter data in the log 120/120', such as every two weeks. This is not strictly necessary however, and algorithm 160 could run on command (such as wirelessly received from an external device), or automatically upon the occurrence of certain events in the IMD 10 (completion of a charging session, certain failure modes, etc.).

The values for the present capacity-relevant parameters 120' are queried by the algorithm 160, which the algorithm may determine from log 120 at this point if not determined and stored in advance. Then, percent changes in battery capacity warranted for each of these values are determined using battery capacity database 122, as explained earlier. Actual values for the percent changes are provided in FIG. 6A to ease understanding of subsequent processing. Additionally, the weights and priorities for each of the parameters may also be retrieved from the database 122 if present.

Figure 6B:
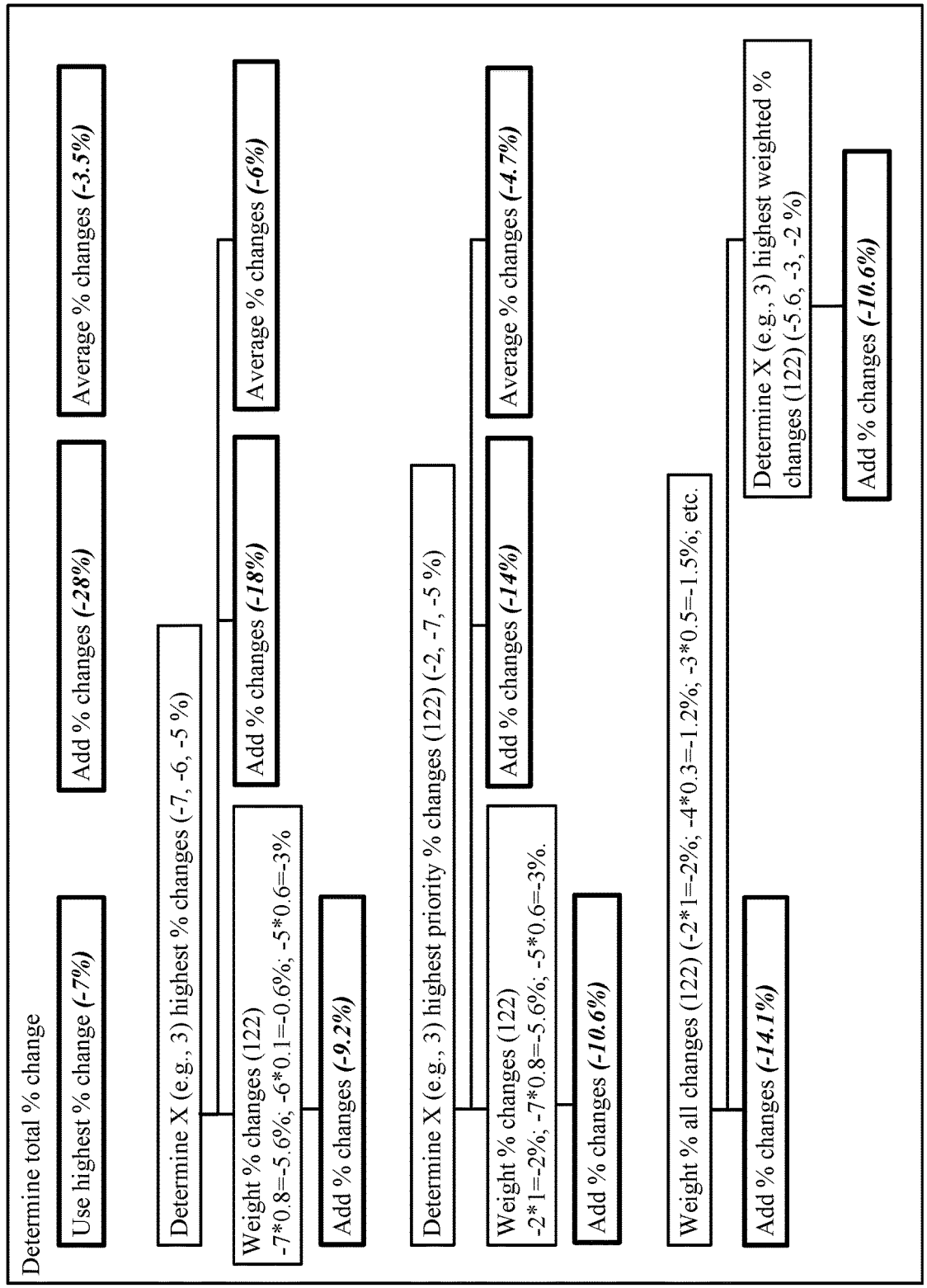

At this point, the algorithm 160 will determine a total percent change in battery capacity, and processing of the data to determine this total can occur in several different ways, some of which are shown in FIG. 6B. For example, the algorithm 160 may just use the largest percentage change (−7%) on the basis that this capacity-relevant parameter is having the largest effect on battery capacity. Alternatively, the algorithm 160 may add (−28%) or average (−3.5%) the determined percentages, so that the effect of each parameter is considered to some extent.

Alternatively, the algorithm 160 may consider only a certain number (e.g., X=3) of the highest determined percentages (−7, −6, −5%), and discard all other lower percentages from subsequent analysis as being too minimal in their effect on battery capacity. These remaining percentages can then be added (−18%) or averaged (−6%) as before. Alternatively, these remaining percentages can be weighted using the retrieved weights (if present), and added (−9.2%).

Alternatively, the algorithm 160 may consider only a certain number (e.g., X=3) of the determined percentages (−2, −7, −5%) having the highest priorities (1, 2, and 3), if such data is present. These percentages may then be added (−14%), averaged (−4.7%), or weighted and added (−10.6%) as described in the preceding paragraph.

In yet another example, the algorithm 160 may weight all of the determined percentages, if such weight data is present. These resulting weighted percentages may be then be added (−14.1%). This may comprise a most preferred manner of processing the percentages, as all are considered, with capacity-relevant parameters of lesser relevance having a smaller effect on the total percent change. Alternatively, only the most relevant of the weighted percentages may be further considered (−5.6, −3, −2%) and added (−10.6%).

All of these alternatives for processing the determined percentages to arrive at a total percentage change indicative of the overall change in battery capacity have some reasonable basis. Still other ways of processing the capacity-relevant parameters are possible, depending on manufacturer preferences and experience.

The total percentage comprises (or at least correlates to) an estimation of the battery capacity, which can be stored in an estimated capacity log 162 (FIG. 4) associated with the EOL algorithm 160 along with a timestamp tx denoting when the estimation occurred, as shown in FIG. 6C. Note the previously-estimated battery capacities and their timestamps are also included in the log 162. In short, estimated capacity log 162 records the battery capacity as estimated by the algorithm 160 as a function of time.

In a next step of the EOL algorithm 160, a forecasting/determination algorithm 164 (FIG. 4) is run, which preferably (but not necessarily) uses the estimated capacity log 162 as its input. The algorithm 164 may curve fit the entries in the estimated capacity log 162 (e.g., using a least squares analysis) to extrapolate estimated battery capacity as a function of time. As shown in FIG. 4, the algorithm 164 can also receive as inputs thresholds to assist in the analysis of the estimated battery capacities, such as a threshold capacity, Cap(th), which is used to forecast (and ultimately) determine tEOL, and tGRACE, which represents a grace period prior to tEOL at which the early replacement indicator is determined (tEOLi), as discussed further below.

Figure 6E:
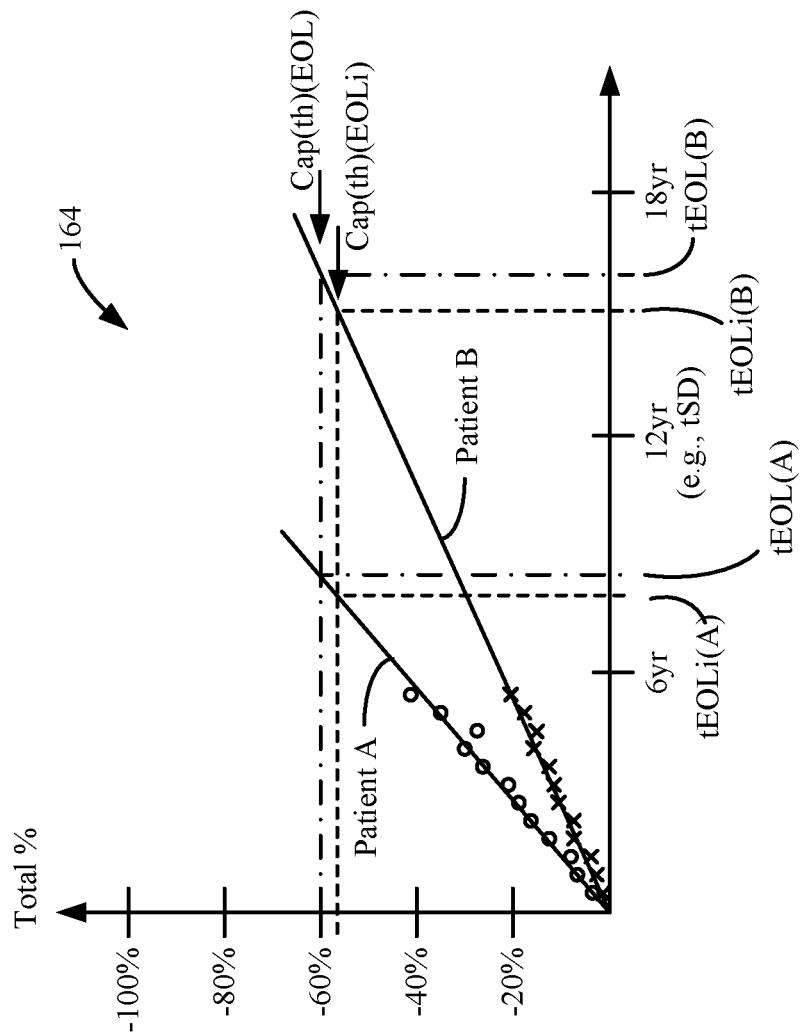
Figure 6E:
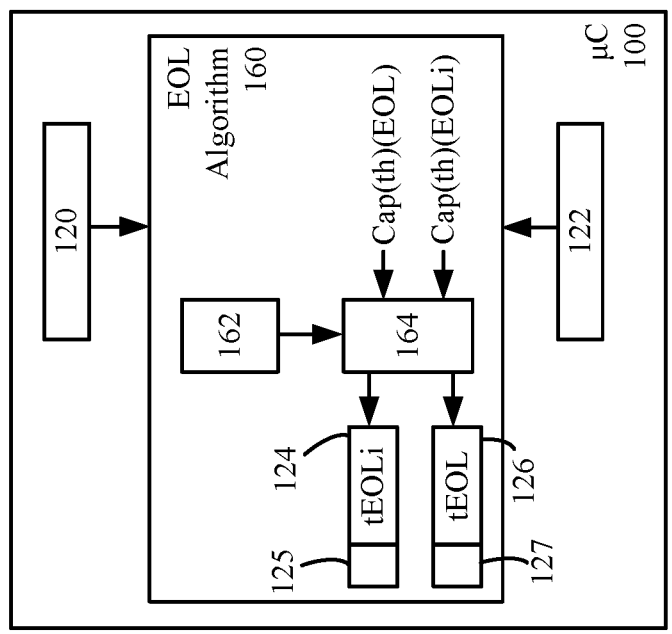

Operation of the forecasting/determination algorithm 164 and the relevance of these thresholds are illustrated graphically in FIG. 6D. Shown are the estimated battery capacities as a function of time (e.g., from log 162) for two patients A and B. As discussed, these data points can be curve fit, and the point at which the extrapolated curves cross Cap(th) forecasts tEOL for the two patients (tEOL(A), tEOL(B)). Once forecasted, tEOL can be stored for the respective patients in their EOL registers 126. tGRACE can represent a fixed time period, such as six months, before the forecasted issuance of tEOL, so a forecasted tEOLi (i.e., tEOLi=tEOL−tGRACE) can be also be stored in EOLi registers 124 for both patients. As shown, patient A comprises a strenuous-use IMD patient, and thus his forecasted values for tEOLi and tEOL are smaller than light-use IMD patient B.

tEOLi can be forecasted in other manners, and independently of tEOL. For example, as shown in FIG. 6E, forecasting/determination algorithm 164 forecasts and determines tEOLi using its own capacity threshold, Cap(th) (EOLi), different from the higher threshold, Cap(th)(EOL), used to forecast and determine tEOL. Note that this alternative algorithm 164 results in forecasts for tEOLi and tEOL that may not be spaced at a fixed interval, as FIG. 6E shows.

Threshold Cap(th) (FIG. 6D), or thresholds Cap(th) (EOLi) and Cap(th)(EOL) (FIG. 6E), are preferably programmed into the IMD 10 as part of the EOL algorithm 160 by the manufacturer, with such threshold(s) being set based on manufacturer preferences and experience. As shown in FIG. 6D, the EOL threshold has been set to −60%, meaning the point at which the rechargeable battery 36 has lost 60% of its capacity. In FIG. 6E, the EOLi threshold is slightly lower, about −56%. Like the estimated capacities in log 162 themselves, these capacity thresholds may not exactly equal the actual battery capacity, but will nonetheless correlate to the actual battery capacity, and thus can be empirically set at a point where rechargeable battery performance is no longer sufficient for reasonable operation—e.g., when the time needed to recharge the battery starts to rival the time that the IMD is used to provide therapy. Note that Cap(th) and Cap(th)(EOL) may be set conservatively to assure that a small amount of capacity remains in case the IMD needs power, for example, to provide telemetry even if the battery capacity is too low for the IPG to provide therapy.

It is not strictly necessary that the forecasting/determination algorithm 164 use the estimated capacity log 162 to forecast or determine tEOLi or tEOL, and in fact it is not necessary that previously-estimated battery capacities be stored in association with the EOL algorithm 160 at all, although this is preferable and convenient. Instead, algorithm 164 can operate directly on some or all of the parameters as stored over time in the capacity-relevant parameter log 120 (FIG. 5A) and the battery capacity database 122 (FIG. 5C). Having said this, such direct analysis of the log 120 may be require significance computational power, and thus the intermediate steps of determining the present capacity-relevant parameters 120' (FIG. 5B), populating the estimated capacity log 162 (FIG. 6C), etc. are preferred.

Referring again to FIG. 6A, once tEOL and tEOLi are forecasted, their values can be stored in registers 126 and 124 (FIG. 4). Note that tEOL and tEOLi might have been forecasted and stored in registers 126 and 124 upon a previous run of the algorithm 160. If desired, the newly-forecasted (and presumably more accurate) values for tEOLi and tEOL can be added to registers 124 and 126 while still keeping older values, or these older values can be overwritten.

At this point, algorithm may assess whether tEOLi has been determined, which can entail determining whether the current time is after tEOLi as forecasted. If not, the algorithm ends at this point, and the algorithm of FIG. 6A will continue to be used in the future, until tEOLi is determined. If so, the EOLi indicator bit 125 is set, which informs the algorithm 160 that new values for tEOLi should not again be forecasted or stored in EOLi register 124 during future runs of the algorithm 160. Register 124 thus preserves the time at which EOLi was reached.

Once tEOLi is determined, the IPG 10 may hold tEOLi (124), the EOLi indicator (125), and/or the forecasted tEOL (126), and preferably all of these, in a manner flagging them as priority data to be sent to an external device once the external device initiates a communication session with the IPG 10, essentially in the same manner discussed with respect to the tSDi indicator in the Background. Prior to determining tEOLi, the algorithm 160 may not necessarily take steps to transmit tEOLi or tEOL as forecasted to the external device, because battery capacity is not yet of concern. Nonetheless, these forecasted values are still stored (126, 124), and can be read from the IMD 10 at the command of an external device.

The external device receiving these indications and relaying them to the patient could comprise an external charger 90 (FIG. 2), in which case these indications would be sent by LSK telemetry using LSK modulation circuitry 45 (FIG. 2). As this means of telemetry is relatively simple, and because external chargers may have only simple user interfaces, only the EOLi indicator (125) may be telemetered. Upon receipt of the EOLi indicator, the external charger 90 can alert the user in any number of ways, such as by uniquely lighting LED(s) on the case of the external charger or "beeping" of the external charger's speaker.

Alternatively, a more-sophisticated device may initiate a communication session with the IMD 10, such as a patient external controller or a clinician's programmer. Such external devices typically have graphical user interfaces with displays, and so all of tEOLi, the EOLi indicator, and the tEOL forecast are preferably telemetered and indicated on the display. As with the tSDi indicator discussed earlier, this can involve the use of the IMD's telemetry coil 42 and associated telemetry circuitry 43 (FIG. 2). Such means of telemetry may employ Frequency Shift Keying (FSK), and can occur via magnetic induction or by Radio Frequency telemetry (if the IMD 10 has an RF antenna; not shown).

If the external device receiving these indications has broader connectivity, such as to the Internet, or if the IMD 10 itself has such connectivity, such indications may also be sent to the patient's clinician or to the manufacturer. As discussed earlier, the manufacturer could use such data to better understand their warranty and support obligations, which may have changed from those otherwise specified as a default (e.g., a 12-year warranty). For example, if warranty and support are made contingent on tEOL, understanding when tEOL was determined or is forecasted to issue is beneficial for the manufacturer and/or its service representatives to know.

Once tEOLi is determined (e.g., bit 125 set), the algorithm of FIG. 6A is not used in the future. Instead, future execution of the algorithm 160 will occur as set forth in FIG. 7. As noted earlier, the portion of the algorithm set forth in FIG. 7 seeks to forecast (or update the forecast of) tEOL, and to assess whether tEOL has been determined and thus that EOL indication bit 127 can be set.

FIG. 7 is similar to FIG. 6A, although focusing on EOL only, EOLi having already been determined. Thus as shown, the algorithm 160 as before retrieves the capacity-relevant parameters logs 120/120' and consults the battery capacity database 122; determines the percentage change for each parameter; retrieves the weight/priority for each parameter is present and used; and processes those percentages to determine an estimated total percentage change to the battery capacity, which is stored in estimated capacity log 162. Forecasting/determination algorithm 164 again operates to forecast tEOL, which is stored in register 126. (Note that algorithm 164 at this point need not consider thresholds relevant to EOLi, such as tGRACE (FIG. 6D) or Cap(th) (EOLi) (FIG. 6E). That is, only Cap(th) (FIG. 6D) or Cap(th)(EOL) (FIG. 6E) are used). If tEOL is not determined, the algorithm 160 ends and the algorithm of FIG. 7 is used again until the tEOL determination is made. When tEOL is determined in the future, EOL indicator bit 127 is set, and tEOL (126) and/or its indication (127) are telemetered at one or more future communication or charging sessions. Once tEOL has been determined, the algorithm 160 has largely served its purpose, and its use may be discontinued.

As noted earlier, the shutdown time tSD and its early indicator tSDi may still be included and used in the IMD 10 in conjunction with the tEOLi and tEOL forecasts and determinations provided by the EOL algorithm 160. Alternatively, tEOLi and tEOL may supplant the function of tSDi and tSD, and thus be used to indicate and shutdown operation of the IMD 10, in which case tSDi and tSD would be unnecessary.

Figure 8:
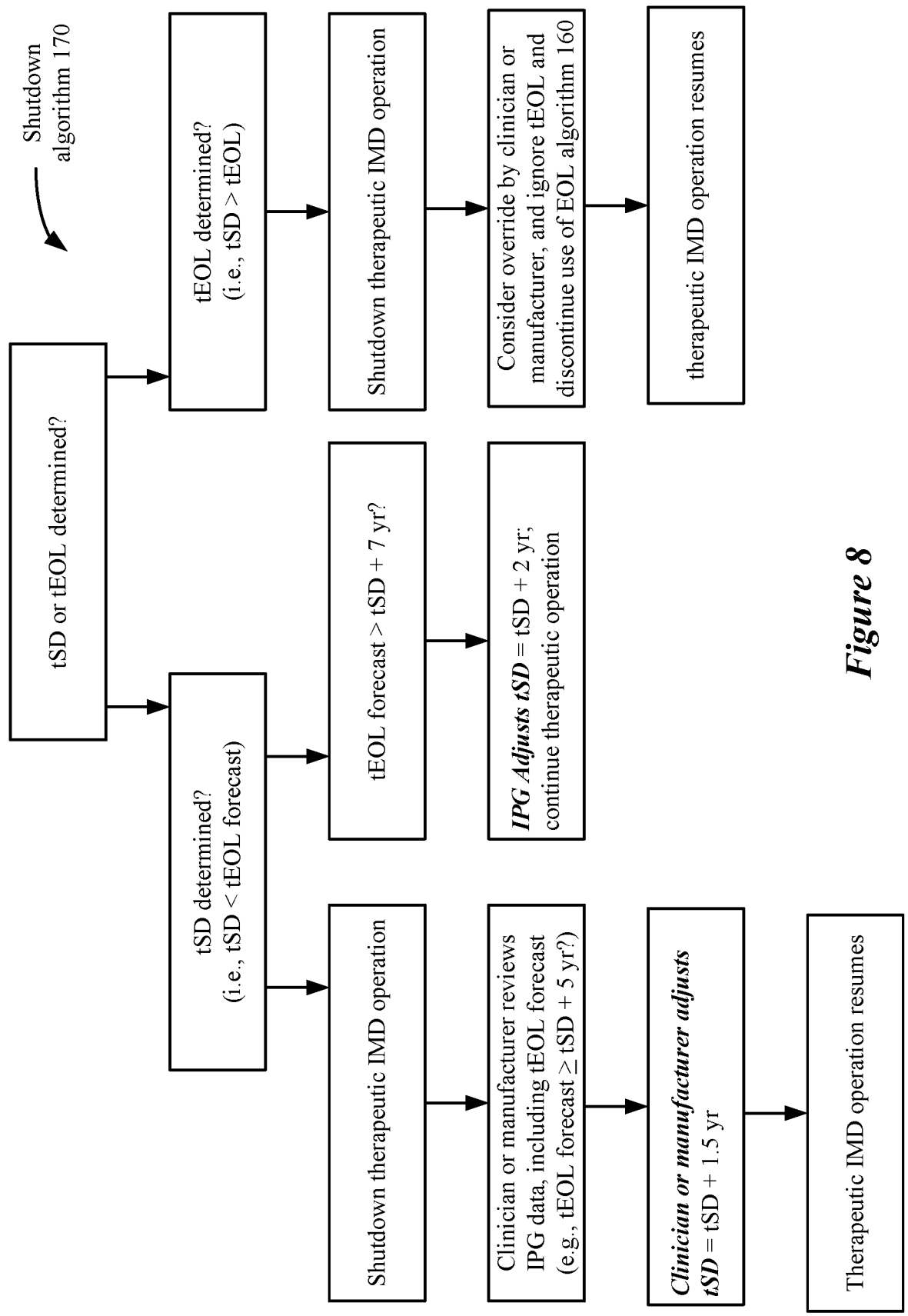
FIG. 8 shows a shutdown algorithm useable in conjunction with tEOL and tSD to determine when to suspend IPG therapeutic operation.

It is still possible and perhaps preferable to include use of the shutdown time tSD in the improved IMD employing the EOL algorithm 160. One manner in which this can occur is shown in FIG. 8, which illustrates use of a shutdown algorithm 170 for suspending therapeutic operation of the IMD 10. As shown in FIG. 4, the shutdown algorithm 170 receives tSD and tEOL from registers 115 and 126 as its inputs. Earlier indicators of these values, such as tSDi and tEOLi, are not necessary to consider, but could be in other embodiments.

As shown, the shutdown algorithm 170 begins to operate when either tSD or tEOL are determined to have occurred. If tEOL has been asserted first, tSD would be later in time that tEOL (see strenuous-use IMD patient A in FIG. 6D). In response, the shutdown algorithm 170 preferably suspends therapeutic operation of the IMD 10. In effect, the determination of tEOL—i.e., the indication that the battery capacity has now degraded to an impermissible degree, and thus has truly reached its end of life—trumps the preset value for tSD. As noted earlier, this information, which may be wirelessly transmitted to the manufacturer, may operate to limit the manufacturer's warranty and service obligations.

In this scenario, there may be good reasons to override the shutdown algorithm 170's ability to use tEOL to shut down therapeutic operation of the IMD, particularly if tSD has not been reached. For example, if an IPG patient is too ill to undergo an explanation procedure, it may be reasonable to continue to let the patient use the IMD, particularly if it seems to be working adequately (despite exceeding tEOL). In this case, a clinician or the manufacturer could decide that the EOL algorithm 160 should be overridden, i.e., that tEOL should be ignored by the shutdown algorithm 170. The clinician or manufacturer could so override tEOL using their more-sophisticated external devices, which unlike the patient external controller would have authority to access and change operation of the EOL algorithm 160. Overriding tEOL may be particularly reasonable in such special cases, particularly when one notes that the computation of tEOL is based on assumptions, and thus that tEOL does not perfectly predict end of IMD life.

If tSD has been asserted first at the start of the shutdown algorithm 170, tEOL has not been determined, and is at this point merely forecasted as stored in register 126 (see light-use IPG patient B in FIG. 6D). In this case, tEOL may suggest that the IMD is working fine for this patient (at least from a battery capacity perspective), and therefore that it may be reasonable for the patient to continue to use the IMD for a longer time.

If so, tSD may be adjusted to a later time by overwriting tSD in register 115. In one simple option not illustrated, tSD could simply be adjusted to the forecasted value for tEOL, either automatically by the IPG, or by a clinician or manufacturer. However, because tEOL is merely a forecast resting on assumptions, such a strategy for adjusting tSD and extending IMD life runs the risk of placing tSD too far in the future beyond the time at which the IMD's life actually ends.

More conservative options for this scenario are thus illustrated in FIG. 8. In one option, the IPG 10 itself can adjust tSD via the shutdown algorithm 170. It is preferred that this option would only be used in situations where tEOL as forecasted is well beyond tSD, by 7 years in the illustrated example. Should this criteria be met, the shutdown algorithm 170 may increase tSD by some additional amount to allow therapeutic use of the IMD to continue. In one example, tSD could be increased by the full difference between tEOL as forecasted and tSD. This is akin to setting tSD to the forecasted tEOL, which as noted above may be of concern. Thus, a more preferred option would be to allow the shutdown algorithm 170 to automatically increase tSD by a lesser amount, such as 2 years as illustrated, or by some fraction of the full difference (e.g., k*(tEOL forecast–tSD), where 0<k<1). As noted above, should tSD be adjusted upwards in this manner, the manufacturer may extend its warranty and support obligations. Alternatively, the manufacturer may still only warrant and support the IMD up to tSD. In effect, the patient could continue to use her IMD, but the manufacturer may thereafter be free of continued responsibility.

Another conservative option illustrated in the scenario where tSD has been reached, but tEOL has not, is to simply suspend operation of the IMD. In effect, tSD trumps tEOL for safety or liability reasons. However, such suspension of operation may not be permanent, and therapeutic operation can commence later pursuant to the discretion of the clinician or manufacturer. Even though the IMD is at this point not providing stimulation therapy for example, it is still preferably capable of powering housekeeping functions such as telemetry. The clinician or manufacture may thus download data from the IMD for review, including the forecasted tEOL in register 126. Upon qualitative review of such data, including an understanding of the patient's history and needs, the clinician or manufacturer may decide to adjust tSD in register 115 (using an external clinician's programmer) by an amount with which they are comfortable, such as 1.5 years in the illustrated example. It would be expected that such increase would again conservatively less than the amount fully suggested by tEOL (as illustrated in this example, 5 years), for the reasons described above. And again, extending tSD may have warranty and support implications.

Although not illustrated, tSD may in some cases be adjustable downward (i.e., tSD in register 115 overwritten) to a lower time. This could be useful if tEOL as forecasted would occur before TSD, such as in the case of the strenuous-use IPG patient B.

It should be noted that the illustrated order of the steps performed in EOL algorithm 160 and the shutdown algorithm 170 are merely examples, and changes could be made to the disclosed order in manners not affecting its overall results. Additionally, not all steps are strictly necessary, and other steps could be included as well.

While algorithm 160 has been disclosed as forecasting and determining both tEOLi and tEOL, it should be noted that the algorithm 160 can instead be used to forecast and determine one of these values. Likewise, algorithm 160 can also be used to only forecast these values without determining when they are reached, or only to determine when they are reached without forecasting.

While forecasting and determination of tEOLi and tEOL has been illustrated for completeness as potentially involving analysis of several different capacity-relevant parameters, which can be weighted, mathematically combined, etc. it should be noted that the use of even a single capacity-relevant parameter reviewed over some portion of the IMD's life is sufficient to implement the disclosed EOL algorithm, and to determine and forecast tEOLi and tEOL in a rechargeable-battery IMD.

Although various logs, databases, registers, and algorithms in FIG. 4 are shown as programmed into the memory of the microcontroller 100, they could instead reside outside of the microcontroller 100 and made accessible to the EOL algorithm 160 and shutdown algorithm 170, which would typically operate in the microcontroller 100.

Although particular embodiments of the present invention have been shown and described, it should be understood that the above discussion is not intended to limit the present invention to these embodiments. It will be obvious to those skilled in the art that various changes and modifications may be made without departing from the spirit and scope of the present invention. Thus, the present invention is intended to cover alternatives, modifications, and equivalents that may fall within the spirit and scope of the present invention as defined by the claims.

What is claimed is:

1. A system, comprising:
an implantable medical device comprising a rechargeable battery and control circuitry, wherein the control circuitry is configured to estimate a capacity of the rechargeable battery at different points in time during operation of the implantable medical device and configured to determine at least one first parameter during each previous charging session of the rechargeable battery, wherein each of the capacities are estimated using the determined at least one parameter, wherein the control circuitry is further configured to determine a forecasted end of life of the implantable medical device using the estimated capacities; and
an external device configured to receive and display the forecasted end of life of the implantable medical device.

2. The system of claim 1, further comprising an external charger configured to wirelessly charge the rechargeable battery of the implantable medical device.

3. The system of claim 1, wherein the external device comprises a patient external controller.

4. The system of claim 1, wherein the external device comprises a clinician's programmer.

5. The system of claim 1, wherein the implantable medical device further comprises telemetry circuitry configured to telemeter the forecasted end of life to the external device.

6. The system of claim 5, wherein the telemetry circuitry is configured to telemeter the forecasted end of life upon receipt of a command from the external device, or when the external device initiates a communication session with the implantable medical device.

7. The system of claim 1, wherein the control circuitry is further configured to suspend therapeutic operation of the implantable medical device when the forecasted end of life has been reached.

8. The system of claim 1, wherein the control circuitry is configured to store a shutdown time at which therapeutic operation of the implantable medical device is normally suspended.

9. The system of claim 8, wherein if the stored shutdown time has been reached and is earlier than the forecasted end of life, the control circuitry is further configured to extend therapeutic operation of the implantable medical device beyond the shutdown time.

10. The system of claim 8, wherein if the stored forecasted end of life has been reached and is earlier than the shutdown time, the control circuitry is further configured to suspend therapeutic operation of the implantable medical device.

11. The system of claim 1, wherein the forecasted end of life is determined as a time at which the rechargeable battery is expected to reach a capacity threshold.

12. The system of claim 1, wherein the control circuitry is further configured to determine a forecasted early replacement indicator for the implantable medical device that precedes the forecasted end of life, and wherein the external device is configured to receive and display the forecasted early replacement indicator for the implantable medical device.

13. The system of claim 12, wherein the control circuitry is configured to determine the forecasted early replacement indicator using the estimates of the capacity of the rechargeable battery at the different points in time during operation of the implantable medical device.

14. The system of claim 13, wherein the implantable medical device further comprises telemetry circuitry configured to telemeter the forecasted early replacement indicator to the external device.

15. The system of claim 12, wherein the forecasted early replacement indicator is determined as a first time at which the rechargeable battery is expected to reach a first capacity threshold.

16. The system of claim 15, wherein the forecasted end of life is determined as a second time later than the first time at which the rechargeable battery is expected to reach a second capacity threshold.

17. The system of claim 12, wherein the early replacement indicator is forecasted using the forecasted end of life.

18. The system of claim 17, wherein the forecasted early replacement indicator comprises a set time before the forecasted end of life.

19. The system of claim 1, wherein the at least one first parameter comprises one or more of a number of the previous charging sessions of the rechargeable battery, a voltage of the rechargeable battery at the start of at least one previous charging session, a voltage of the rechargeable battery at the end of at least one previous charging session, a duration of at least one previous charging session, a charge provided to the rechargeable battery during at least one previous charging session, a discharge depth comprising a difference between a voltage of the rechargeable battery at the start and finish of at least one previous charging sessions, and a battery charging current provided to the rechargeable battery during at least one previous charging sessions.

20. The system of claim 1, wherein the capacities are further estimated using at least one second parameter determined during previous use of the implantable medical device to provide therapy between the previous charging sessions, and/or an age of the rechargeable battery.

* * * * *